United States Patent [19]

Nagano et al.

[11] Patent Number: 5,366,955

[45] Date of Patent: Nov. 22, 1994

[54] PYRIMIDONE DERIVATIVES AND THEIR USE

[75] Inventors: Eiki Nagano, Raleigh, N.C.; Susumu Takemura, Takarazuka, Japan; Masayuki Enomoto, Nishinomiya, Japan; Masaharu Sakaki, Toyonaka, Japan; Satoru Kizawa, Takarazuka, Japan

[73] Assignee: Sumitomo Chemical Company, Limited, Osaka, Japan

[21] Appl. No.: 53,399

[22] Filed: Apr. 28, 1993

[30] Foreign Application Priority Data

Apr. 28, 1992 [JP] Japan .................... 4-109860

[51] Int. Cl.$^5$ ................ C07D 498/02; C07D 403/04; C07D 239/22; A61K 31/505
[52] U.S. Cl. .................... 504/225; 504/235; 504/242; 544/105; 544/295; 544/319
[58] Field of Search ........... 544/105, 295, 319; 504/225, 235, 242

[56] References Cited

U.S. PATENT DOCUMENTS

| | | | |
|---|---|---|---|
| 3,823,135 | 7/1974 | Pilgram et al. | 544/319 |
| 3,869,457 | 3/1975 | Lutz et al. | 504/242 |
| 3,981,715 | 9/1976 | Lutz et al. | 504/242 |
| 4,981,508 | 1/1991 | Strunk et al. | 504/242 |
| 5,041,156 | 8/1991 | Suchy et al. | 504/242 |
| 5,077,297 | 12/1991 | Perrior et al. | 514/269 |
| 5,104,878 | 4/1992 | Whittle et al. | 514/269 |
| 5,149,810 | 9/1992 | Perrior et al. | 544/309 |
| 5,232,895 | 8/1993 | Suchy et al. | 504/243 |

FOREIGN PATENT DOCUMENTS

| | | |
|---|---|---|
| 0260621 | 3/1988 | European Pat. Off. |
| 0338686 | 10/1989 | European Pat. Off. |
| 0396250 | 11/1990 | European Pat. Off. |
| 0420194 | 4/1991 | European Pat. Off. |
| 0481604 | 4/1992 | European Pat. Off. |

OTHER PUBLICATIONS

Chemical Abstracts 115(3) 29371a, Abstract of JP02306968 AZ Dec. 20, 1990.

*Primary Examiner*—Mukund J. Shah
*Assistant Examiner*—Matthew V. Grumbling
*Attorney, Agent, or Firm*—Birch, Stewart, Kolasch & Birch

[57] ABSTRACT

There are disclosed novel pyrimidone derivatives of the formula I:

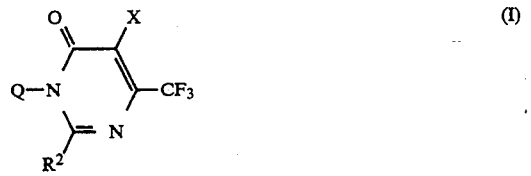

wherein X is hydrogen, chlorine, methyl or ethyl, $R^2$ is hydrogen or methyl, and Q is

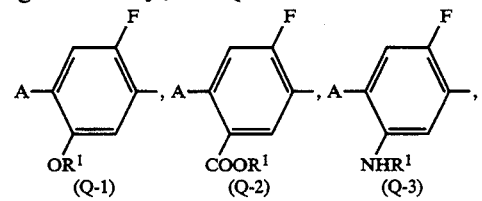

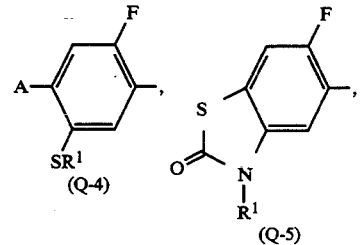

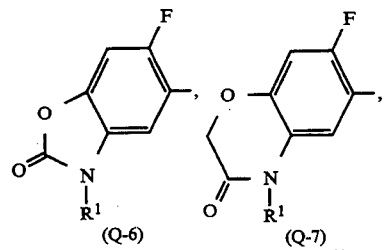

(Abstract continued on next page.)

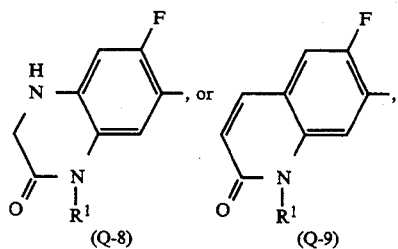

A is fluorine, chlorine or bromine; and $R^1$ is alkyl, alkenyl, alkynyl, alkoxyalkyl or haloalkyl.

Also disclosed are a herbicidal composition containing a herbicidally effective amount of the compound (I) as an active ingredient and a method for exterminating undesired weeds by applying a herbicidally effective amount of the compound (I) to an area where the undesired weeds grow or will grow.

18 Claims, No Drawings

PYRIMIDONE DERIVATIVES AND THEIR USE

The present invention relates to novel pyrimidone derivatives and herbicidal compositions containing them as active ingredients. It is known that certain kinds of pyrimidone derivative can be used as active ingredients of herbicides (see, e.g., U.S. Pat. No. 3,823,135 and U.S. Pat. No. 3,869,457).

These compounds, however, have insufficient herbicidal activity and poor selectivity between crop plants and weeds, and it cannot always be said that they are satisfactory for active ingredients of herbicides.

Under these circumstances, the present inventors have intensively studied various compounds. As the result, we have found that particular kinds of pyrimidone derivatives have excellent herbicidal activity and excellent selectivity between crop plants and weeds, thereby completing the present invention.

That is, the present invention provides novel pyrimidone derivatives of the formula:

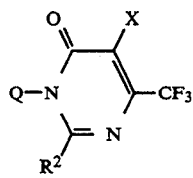

(I)

wherein $R^2$ is hydrogen or methyl; X is hydrogen, chlorine, methyl or ethyl; Q is of the formula:

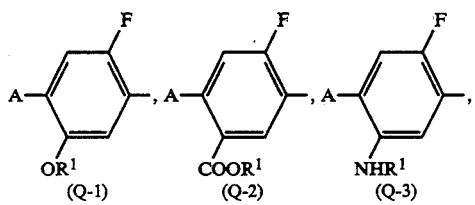

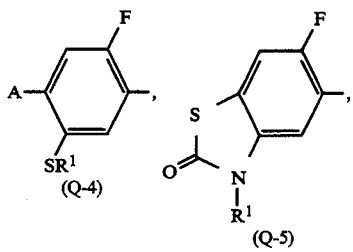

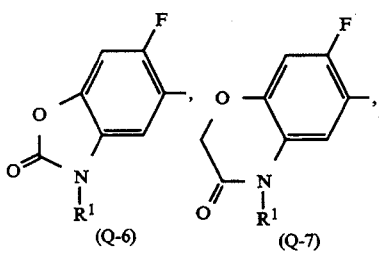

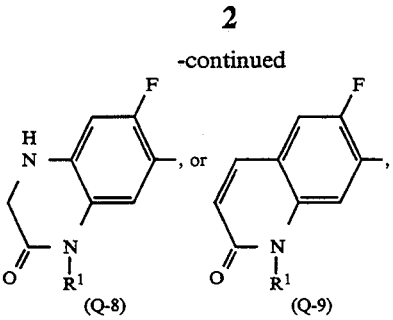

A is fluorine, chlorine or bromine; and $R^1$ is alkyl, alkenyl, alkynyl, alkoxyalkyl or haloalkyl.

As used herein, the term "alkyl" refers to, for example, $C_1$–$C_6$ alkyl such as methyl, ethyl,-n-propyl, i-propyl, n-butyl, i-butyl, sec-butyl, n-pentyl and n-hexyl; the term "alkenyl" refers to, for example, $C_2$–$C_6$ alkenyl such as 2-propenyl and 1-methyl-2-propenyl; the term "alkynyl" refers to, for example, $C_2$–$C_6$ alkynyl such as propargyl and 1-methylpropargyl; the term "alkoxyalkyl" refers to, for example, alkoxyalkyl containing from 2 to 6 carbon atoms, such as methoxymethyl and ethoxymethyl; and the term "haloalkyl" refers to, for example, $C_1$–$C_6$ alkyl substituted with one or more halogen atoms including fluorine, chlorine and bromine, such as fluoroethyl and chloroethyl.

The present invention also provides a herbicidal composition comprising a herbicidally effective amount of the compound (I) as an active ingredient and a method of exterminating undesired weeds by applying a herbicidally effective amount of the compound (I) to an area where the undesired weeds grow or would grow.

Among the compounds (I) wherein Q is of the formula (Q-1), (Q-2), (Q-3) or (Q-4), preferred are those wherein A is chlorine. Among the compounds (I), preferred are those wherein Q is of the formula (Q-1), (Q-2), (Q-5) or (Q-7); more preferred are those wherein Q is of the formula (Q2) and $R^1$ is $C_2$–$C_4$ alkyl and those wherein Q is of the formula (Q-1), (Q-5) or (Q-7) and $R^1$ is $C_1$–$C_4$ alkyl, $C_2$–$C_4$ alkenyl or $C_2$–$C_4$ alkynyl. Among these more preferred compounds, more preferred are those wherein Q is of the formula (Q-1), (Q-5) or (Q-7); still more preferred are those wherein Q is of the formula (Q-5) or (Q-7); and particularly preferred are those wherein Q is of the formula (Q-7).

Among the compounds (I), preferred are those wherein $R^2$ is methyl.

Among the compounds (I), preferred are those wherein X is hydrogen, chlorine or methyl; more preferred are those wherein X is chlorine or methyl; and still more preferred are those wherein X is methyl.

Still more preferred are those which have a combination of $R^2$, X and Q as described above.

Typical examples of the compound (I) are 5-chloro-3-(7-fluoro3,4-dihydro-3-oxo-4-propargyl-2H-1,4-benzoxazin-6-yl)-6-trifluoromethylpyrimidin-4-one, 3-(7-fluoro-3,4-dihydro-3-oxo-4-propargyl-2H-1,4-benzoxazin-6-yl)-5-methyl-6-trifluoromethylpyrimidin-4-one, 3-(6-fluoro-2-oxo-3-isopropylbenzothiazolin-5-yl)-5-methyl-6-trifluoromethylpyrimidin-4-one and 3-(4-chloro-2-fluoro-5-isopropoxycarbonylphenyl)-5-methyl-6-trifluoromethylpyrimidin-4-one.

The following will describe some production processes for the compound (I).

<Production Process (a)>

The compound (I) can be produced through the following reaction scheme.

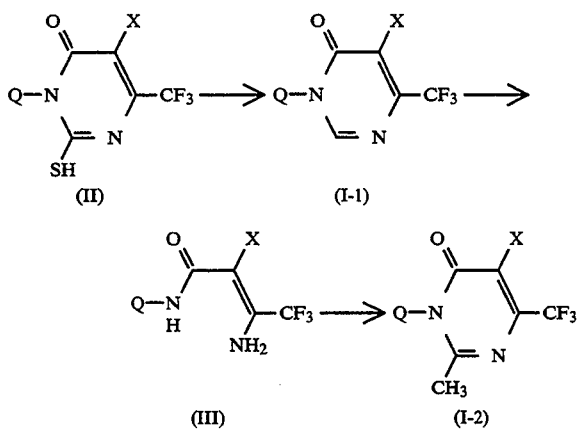

wherein Q and X are each as defined above. The compound (I-1) can be produced by reducing the compound (II) with Raney nickel.

The reaction is usually carried out in an inert solvent in the presence of a base at a temperature of 0° to 200° C. for a period of 0.5 to 96 hours.

The Raney nickel and the base are used in the respective amounts of not less than one equivalent to one equivalent of the compound (II); when necessary, they may be used in large excess.

Examples of the inert solvent are aliphatic hydrocarbons such as hexane, heptane, ligroin and petroleum ether; aromatic hydrocarbons such as benzene, toluene and xylene; ethers such as diethyl ether, diisopropyl ether, dioxane, tetrahydrofuran and diethyleneglycol dimethyl ether; alcohols such as methanol, ethanol, isopropanol, t-butanol, octanol, cyclohexanol, 2-methoxyethanol, diethyleneglycol and glycerol; nitriles such as acetonitrile and isobutylonitrile; acid amides such as formamide, N,N-dimethylformamide and acetamide; liquid ammonia and water. These solvents may be used solely or in combination.

Examples of the base are organic bases such as pyridine, triethylamine and N,N-diethylaniline; and inorganic bases such as sodium hydroxide, potassium hydroxide, sodium carbonate, potassium carbonate, sodium acetate and ammonia.

After completion of the reaction, undissolved materials in the reaction mixture are removed by filtration or dissolved by addition of an acid to the reaction mixture, and the resultant mixture is subjected to ordinary post-treatment such as extraction with an organic solvent, followed by concentration. If desired, any conventional purification procedure such as chromatography or recrystallization may be applied to the resulting product, thus obtaining the desired compound (I-1).

The compound (III) can be produced by heating the compound (I1) in a solvent in the presence of the secondary amine at a temperature of 40° to 200° C., preferably 60° to 150° C. for a period of 0.5 to 20 hours.

The secondary amine is used in amount of 1 to 5 equivalents to one equivalent of the compound (I-1).

Examples of the secondary amine are diethylamine diisopropylamine, pyrrolidine, piperidine and morpholine.

Examples of the solvent are alcohols such as methanol and ethanol.

The compound (I-2) can be produced by reacting the compound (III) with acetyl chloride in an inert solvent in the presence of a base at a temperature of 10° to 150° C. for a period of 1 to 6 hours. The acetyl chloride and the base are used in the respective amounts of 1 to 2 equivalents to one equivalent of the compound (III).

Examples of the inert solvent are hydrocarbons such as toluene and benzene; halogenated hydrocarbons such as chloroform and carbon tetrachloride; and amines such as pyridine.

Examples of the base are tertiary amines such as triethylamine and diisopropylethylamine; and pyridine analogs such as pyridine and 2,6-lutidine.

After completion of the reaction, the reaction mixture is poured into a saturated aqueous solution of sodium hydrogencarbonate, and the resultant mixture is subjected to ordinary post-treatment such as extraction with an organic solvent, followed by concentration. If, desired, any conventional purification procedure such as chromatography or recrystallization may be applied to the resulting product, thus obtaining the desired compound (I-2).

The compound (II) used in Production Process (a) can be produced by reacting the compound of the formula:

wherein Q is as defined above with a compound of the formula:

wherein $R^3$ is $C_1$–$C_6$ alkyl and X is as defined above, in the presence of sodium hydride at a temperature of −10° to 30° C. for a period of 0.5 to 10 hours.

The compound (V) and the sodium hydride are used in amounts of 1 to 3 equivalents and 1 to 1.3 equivalents, respectively, to one equivalent of the compound (IV).

The compound (IV) can be produced by reacting the aniline derivatives corresponding to the compound (IV) with thiophosgene. The aniline derivative can be produced according to the method as described in, for example, EP-61741-A, JP-60-78959-A, JP61-194074-A, U.S. Pat. No. 4,720,297 and U.S. Pat No. 4,640,707, or it can be produced through the following reaction scheme,

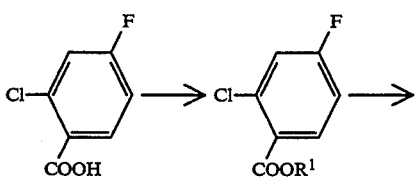

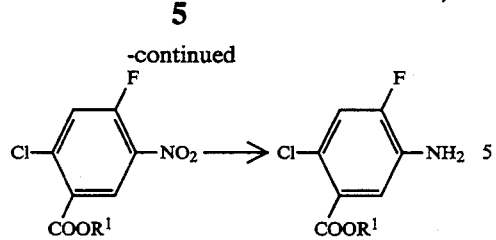

<Production Process (b)>

The compound (I) wherein Q is of the formula (Q-7) can also be produced by reacting the compound of the formula:

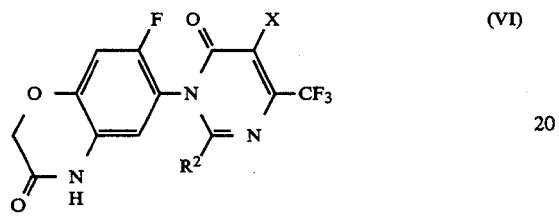
(VI)

wherein $R^2$ and X are each as defined above with a compound of the formula:

$R^1$-Y        (VII)

wherein Y is chlorine, bromine, iodine, alkylsulfonyloxy or arylsulfonyloxy, and $R^1$ is as defined above.

The reaction is usually carried out in an inert solvent in the presence of a base at a temperature of 20° to 200° C. for a period of 0.5 to 96 hours.

The compound (VII) and the base are used in amounts of 1 to 3 equivalents and 1 to 1.2 equivalents, respectively, to one equivalent of the compound (VI).

Examples of the inert solvent are aliphatic hydrocarbons such as hexane, heptane, ligroin and petroleum ether; aromatic hydrocarbons such as benzene, toluene and xylene; ethers such as diethyl ether, diisopropyl ether, dioxane, tetrahydrofuran and diethyleneglycol dimethyl ether; ketones such as acetone, methyl ethyl ketone, methyl isobutyl ketone, isophorone and cyclohexanone; alcohols such as methanol, ethanol, isopropanol, t-butanol, octanol, cyclohexanol, 2-methoxyethanol diethyleneglycol and glycerine; nitriles such as acetonitrile and isobutyronitrile; acid amides such as formamide, N,N-dimethylformamide and acetamide; sulfur compounds such as dimethylsulfoxide and sulphorane; liquid ammonia and water. These solvents may be used solely or in combination.

Examples of the base are organic bases such as pyridine, triethylamine and N,N-diethylaniline; inorganic bases such as sodium hydroxide, potassium hydroxide, sodium carbonate, potassium carbonate, sodium hydride; and alkali metal alkoxides such as sodium methoxide and sodium ethoxide.

After completion of the reaction, the reaction mixture is subjected to ordinary post-treatment. For example, the reaction mixture is poured into water, and the resultant mixture is extracted with an organic solvent, followed by concentration. If desired, any conventional purification procedure such as chromatography or recrystallization may be applied to the resultant product, thus obtaining the desired compound.

The compound (VI) can be produced through the following reaction route 1 or 2.

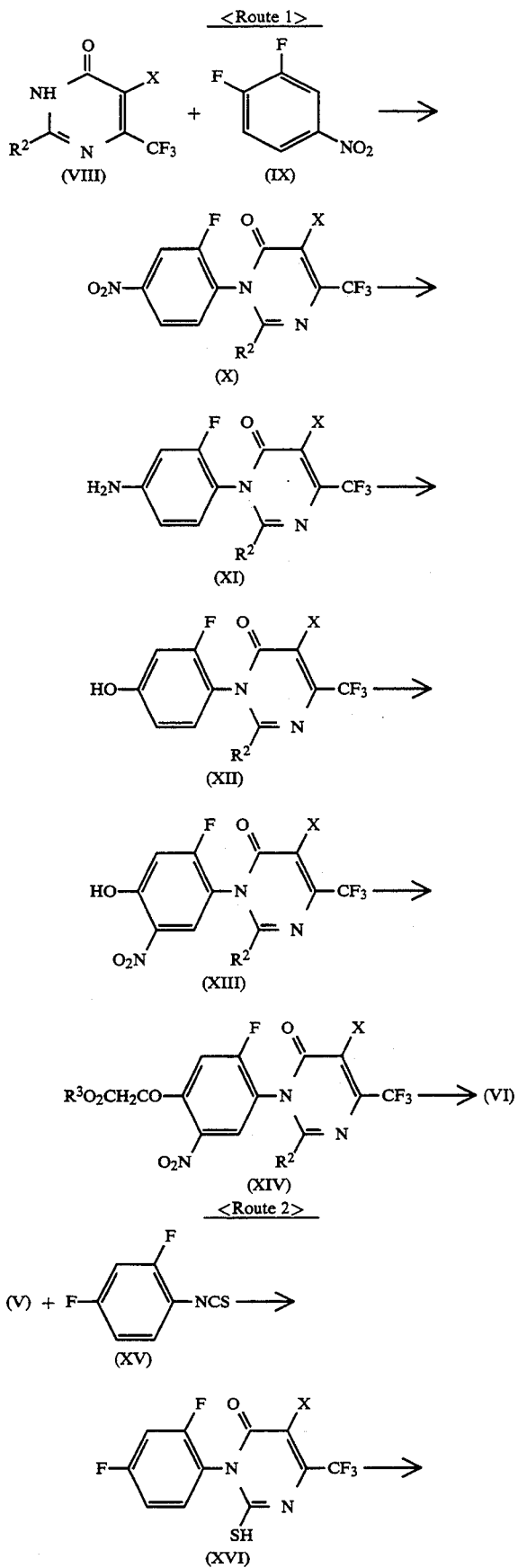

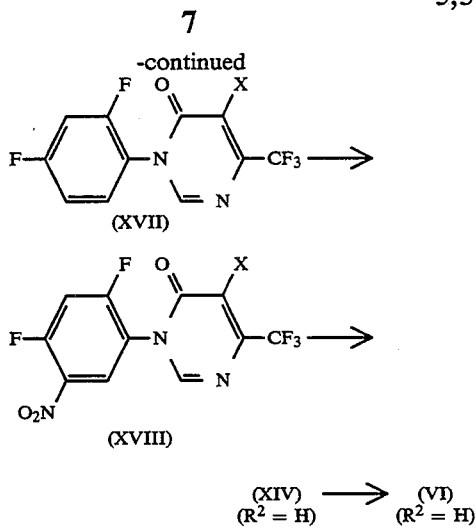

wherein $R^2$, $R^3$ and X are each as defined above.

<Route 1>

Step 1: (VIII)+(IX)→(X)

The compound (X) can be produced by reacting the compound (VIII) with the compound (IX).

The reaction is usually carried out in an inert solvent such as dimethylformamide, dimethylacetamide or N-methylpyrrolidone in the presence of a base such as sodium hydride or potassium hydride at a temperature of −30° to 200° C., preferably 30° to 100° C.

The compound (IX) is used in an amount of 1 to 3 equivalents to one equivalent of the compound (VIII).

The compound (VIII) can be produced according to the method as described in JP-A-2-304066.

Step 2: (X)→(XI)

The compound (XI) can be produced by reducing the compound (X) with 2.5 to 10 equivalents of iron powder to one equivalent of the compound (X) at a temperature of 50° to 150° C.

Step 3: (XI)→(XII)

The compound (XII) can be produced by treating the compound (XI) with one equivalent to a large excess of sulfuric acid to one equivalent of the compound (XI) at a temperature of −10° to 80° C. to form a sulfate salt; reacting the sulfate salt with 1 to 1.5 equivalents of a nitrite salt such as sodium nitrite in a solvent such as water and acetic acid at a temperature of −20° to 10° C. to form a diazonium salt; and then reacting the diazonium salt with a large excess of 10–50% aqueous sulfuric acid at a temperature of 50° to 200° C., preferably 80° to 120° C.

Step 4: (XII)→(XIII)

The compound (XIII) can be produced by reacting the compound (XII) with 1 to 2 equivalents of nitric acid to one equivalent of the compound (XII) without or in an inert solvent such as carbon tetrachloride at a temperature of −10° to 20° C.

Step 5: (XIII)→(XIV)

The compound (XIV) can be produced by reacting the compound (XIII) with a compound of the formula:

$$Z\text{-}CH_2CO_2R^3 \qquad (XIX)$$

wherein Z is halogen and $R^3$ is as defined above.

The reaction is usually carried out in an inert solvent such as dimethylformamide, dimethylacetamide, N-methylpyrrolidone or dimethylsulfoxide in the presence of a base such as sodium hydride, potassium hydride, sodium carbonate or potassium carbonate at a temperature of −10° to 100° C.

The compound (XIX) and the base are used in amounts of 1 to 1.5 equivalents and 1 to 1.2 equivalents, respectively, to one equivalent of the compound (XIII).

Step 6: (XIV)→(VI)

The compound (VI) can be produced by reacting the compound (XIV) with 2.5 to 10 equivalents of iron powder to one equivalent of the compound (XIV) in the presence of an excess of acid such as acetic acid or sulfuric acid at a temperature of 50° to 150° C.

<Route 2>

Step 1: (V)+(XV)→(XVI)

The compound (XVI) can be produced by reacting the compound (XV) with the compound (V) in the presence of sodium hydride at a temperature of −10° to 30° C. for a period of 0.5 to 10 hours.

The compound (V) and the sodium hydride are used in the respective amounts of 1 to 1.3 equivalents to one equivalent of the compound (XV).

Step 2: (XVI)→(XVII)

The compound (XVII) can be produced by desulfurizing the compound (XVI) with Raney nickel in an inert solvent in the presence of one equivalent to a large excess of a base, to one equivalent of the compound (XVI), at a temperature of 0° to 200° C.

Examples of the inert solvent are dioxane, tetrahydrofuran, diethyleneglycol, dimethyl ether, methanol, ethanol, isopropanol, 2-methoxyethanol, diethyleneglycol, glycerol and water.

Examples of the base are pyridine, triethylamine, sodium hydroxide, potassium hydroxide, sodium carbonate, potassium carbonate, sodium acetate and ammonia.

Step 3: (XVII)→(XVIII)

The compound (XVIII) can be produced by nitrating the compound (XVII) with 1 to 2 equivalents of nitric acid or mixed acid to one equivalent of the compound (XVII) at a temperature of −10° to 40° C.

Step 4: (XVIII)→(XIV)

The compound (XIV) can be produced by reacting the compound (XVIII) with a compound of the formula:

$$HOCH_2CO_2R^3 \qquad (XX)$$

wherein $R^3$ is as defined above, in an inert solvent such as dioxane, tetrahydrofuran, toluene or benzene in the presence of potassium fluoride at a temperature of 20° to 200° C.

The compound (XX) and the potassium fluoride are used in amounts of 1 to 1.5 equivalents and 1 to 1.5 equivalents, respectively, to one equivalent of the compound (XVIII).

<Production Process (c)>

The compound of the formula (I) wherein Q is of the formula (Q-1) can be produced by treating a compound of the formula:

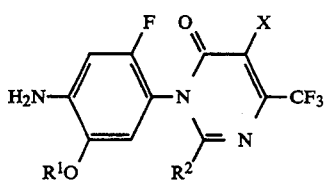

(XXI)

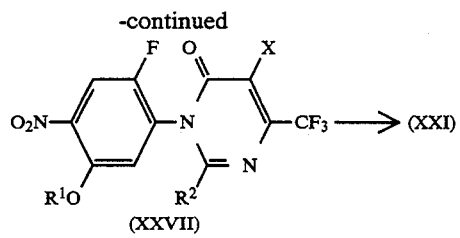

(XXVII)

wherein $R^1$, $R^2$, $R^3$ and X are each as defined above.

Step 1: (XXII)→(XXIII)

The compound (XXIII) can be produced by reacting the compound (XXII) with a compound of the formula:

$$ClCO_2R^3 \qquad (XXVIII)$$

wherein $R^3$ is as defined above in an inert solvent such as water, alcohols or dimethylformamide in the presence of a base such as sodium carbonate or sodium hydroxide at a temperature of $-10°$ to $100°$ C.

The compound (XXVIII) and the base are used in the respective amounts of 1 to 2 equivalents to one equivalent of the compound (XXII).

Step 2: (XXIII)→(XXIV)

The compound (XXIV) can be produced by nitrating with 1 to 2 equivalents of nitric acid or mixed acid to one equivalent of the compound (XXIII) at a temperature of $-10°$ to $20°$ C.

Step 3: (XXIV)→(XXV)

The compound (XXV) can be produced by reacting the compound (XXIV) with the compound (VIII) in an inert solvent such as dimethylformamide, dimethylacetamide or N-methylpyrroidone in the presence of a base such as sodium hydride or potassium hydride at a temperature of $30°$ to $200°$ C.

The compound (VIII) and the base are used in the respective amounts of 1 to 1.5 equivalents to one equivalent of the compound (XXIV).

Step 4: (XXV)→(XXVI)

The compound (XXVI) can be produced by hydrolyzing the compound (XXV) with 1 to 2 equivalents of a base such as sodium hydroxide or potassium hydroxide to one equivalent of the compound (XXV).

Step 5: (XXVI)→(XXVII)

The compound (XXVII) can be produced by reacting the compound (XXVI) with the compound (VII) in the presence of a base such as potassium carbonate at a temperature of $0°$ to $100°$ C.

The compound (VII) and the base are used in the respective amounts of 1 to 2 equivalents to one equivalent of the compound (XXVI).

Step 6: (XVII)→(XXI)

The compound (XXI) can be produced by reducing the compound (XXVII) with 2.5 to 10 equivalents of iron powder to one equivalent of the compound (XXVII) in the presence of an acid such as acetic acid or sulfuric acid at a temperature of $50°$ to $150°$ C.

According to the above production process (a), (b) or (c), various compounds of the formula (I) as shown in Table 1 are obtained.

wherein $R^1$, $R^2$ and X are each as defined above, with 2.5 equivalents to a large excess of 5–30% aqueous hydrochloric acid, to one equivalent of the compound (XXI), without or in a solvent such as acetic acid at a temperature of $10°$ to $80°$ C. to form a hydrochloride salt; reacting the hydrochloride salt with 1 to 1.5 equivalents of an agent for diazotization at a temperature of $-20°$ to $10°$ C. to form a diazonium salt; and treating the diazonium salt with a large excess of hydrochloric acid in the presence of cuprous chloride, cuprous bromide or hydrogen borofluoride (HBF$_4$) at a temperature of $0°$ to $70°$ C., preferably $10°$ to $50°$ C. Examples of the agent for diazotization are nitrite salts such as sodium nitrite and potassium nitrite; and nitrite esters such as isoamyl nitrite.

After completion of the reaction, the reaction mixture is subjected to ordinary post-treatment such as extraction with organic solvent, followed by concentration. If desired, any conventional purification procedure such as chromatography or recrystallization may be applied to the resulting product, thus obtaining the desired compound.

The compound (XXI) can be produced through the following reaction route 3.

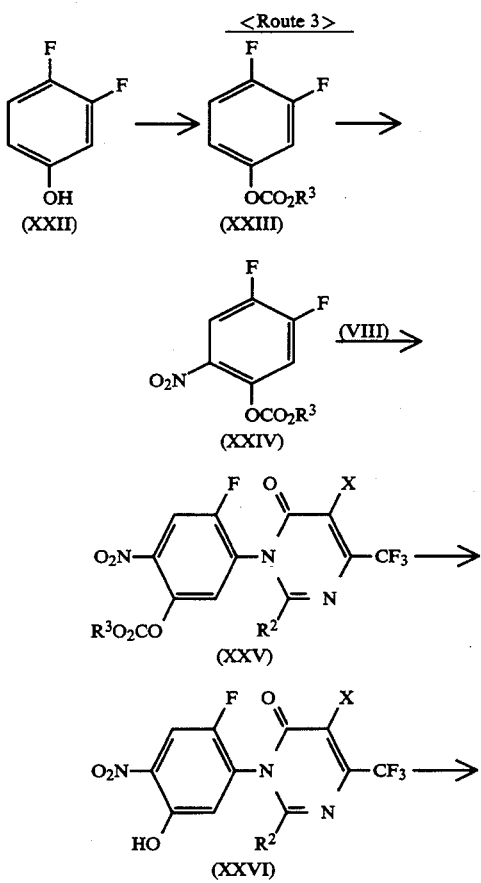

TABLE 1

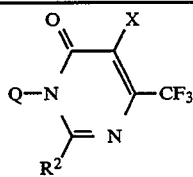

| Compound No. | Q | A | R¹ | R² | X |
|---|---|---|---|---|---|
| 1 | Q-1 | Cl | $CH_3$ | H | H |
| 2 | Q-1 | Cl | $C_2H_5$ | H | H |
| 3 | Q-1 | Cl | $i\text{-}C_3H_7$ | H | H |
| 4 | Q-1 | Cl | $CH_2CH=CH_2$ | H | H |
| 5 | Q-1 | Cl | $CH_2C\equiv CH$ | H | H |
| 6 | Q-1 | F | $CH(CH_3)C\equiv CH$ | H | H |
| 7 | Q-1 | Cl | $CH_2OCH_3$ | H | H |
| 8 | Q-1 | Cl | $CH_2CH_2F$ | H | H |
| 9 | Q-1 | Cl | $CH_2CH_2Cl$ | H | H |
| 10 | Q-1 | Cl | $CH_2CH_2CH_2F$ | H | H |
| 11 | Q-1 | Cl | $CH_3$ | $CH_3$ | H |
| 12 | Q-1 | Cl | $i\text{-}C_3H_7$ | $CH_3$ | H |
| 13 | Q-1 | Br | $CH_2CH=CH_2$ | $CH_3$ | H |
| 14 | Q-1 | Cl | $CH_2C\equiv CH$ | $CH_3$ | H |
| 15 | Q-1 | Cl | $CH_2OCH_3$ | $CH_3$ | H |
| 16 | Q-1 | Cl | $CH_2CH_2F$ | $CH_3$ | H |
| 17 | Q-1 | Cl | $CH_3$ | H | $CH_3$ |
| 18 | Q-1 | Cl | $i\text{-}C_3H_7$ | H | $CH_3$ |
| 19 | Q-1 | Cl | $CH_2CH=CH_2$ | H | $CH_3$ |
| 20 | Q-1 | Cl | $CH_2C\equiv CH$ | H | $CH_3$ |
| 21 | Q-1 | Cl | $CH_2CH_2F$ | H | $CH_3$ |
| 22 | Q-1 | Cl | $i\text{-}C_3H_7$ | $CH_3$ | $CH_3$ |
| 23 | Q-1 | Cl | $CH_2C\equiv CH$ | $CH_3$ | $CH_3$ |
| 24 | Q-1 | Cl | $CH_2OCH_3$ | $CH_3$ | $CH_3$ |
| 25 | Q-1 | Cl | $CH_2C\equiv CH$ | H | Cl |
| 26 | Q-1 | Cl | $CH_2C\equiv CH$ | $CH_3$ | Cl |
| 27 | Q-2 | Cl | $CH_3$ | H | H |
| 28 | Q-2 | Cl | $C_2H_5$ | H | H |
| 29 | Q-2 | Cl | $n\text{-}C_3H_7$ | H | H |
| 30 | Q-2 | Cl | $i\text{-}C_3H_7$ | H | H |
| 31 | Q-2 | Cl | $n\text{-}C_4H_9$ | H | H |
| 32 | Q-2 | Cl | $sec\text{-}C_4H_9$ | H | H |
| 33 | Q-2 | Br | $CH_2C\equiv CH$ | H | H |
| 34 | Q-2 | Cl | $CH_2CH_2CH_2F$ | H | H |
| 35 | Q-2 | Cl | $CH_3$ | $CH_3$ | H |
| 36 | Q-2 | Cl | $C_2H_5$ | $CH_3$ | H |
| 37 | Q-2 | Cl | $i\text{-}C_3H_7$ | $CH_3$ | H |
| 38 | Q-2 | Cl | $CH_3$ | H | $CH_3$ |
| 39 | Q-2 | Cl | $C_2H_5$ | H | $CH_3$ |
| 40 | Q-2 | Cl | $i\text{-}C_3H_7$ | H | $CH_3$ |
| 41 | Q-2 | F | $C_2H_5$ | $CH_3$ | $CH_3$ |
| 42 | Q-2 | Cl | $i\text{-}C_3H_7$ | $CH_3$ | $CH_3$ |
| 43 | Q-2 | Cl | $C_2H_5$ | H | Cl |
| 44 | Q-2 | Cl | $i\text{-}C_3H_7$ | H | Cl |
| 45 | Q-2 | Cl | $i\text{-}C_3H_7$ | $CH_3$ | Cl |
| 46 | Q-3 | Cl | $CH_3$ | H | H |
| 47 | Q-3 | Cl | $C_2H_5$ | H | H |
| 48 | Q-3 | Cl | $n\text{-}C_3H_7$ | H | H |
| 49 | Q-3 | Cl | $i\text{-}C_3H_7$ | H | H |
| 50 | Q-3 | Br | $n\text{-}C_4H_9$ | H | H |
| 51 | Q-3 | Cl | $CH_2CH=CH_2$ | H | H |
| 52 | Q-3 | Cl | $CH_2C\equiv CH$ | H | H |
| 53 | Q-3 | Cl | $CH_2CH_2CH_2F$ | H | H |
| 54 | Q-3 | Cl | $CH_3$ | $CH_3$ | H |
| 55 | Q-3 | Cl | $i\text{-}C_3H_7$ | $CH_3$ | H |
| 56 | Q-3 | Cl | $CH_2C\equiv CH$ | $CH_3$ | H |
| 57 | Q-3 | Cl | $CH_3$ | H | $CH_3$ |
| 58 | Q-3 | Cl | $i\text{-}C_3H_7$ | H | $CH_3$ |
| 59 | Q-3 | Cl | $CH_2C\equiv CH$ | H | $CH_3$ |
| 60 | Q-3 | Cl | $CH_3$ | $CH_3$ | $CH_3$ |
| 61 | Q-3 | Cl | $CH_2C\equiv CH$ | $CH_3$ | $CH_3$ |
| 62 | Q-3 | Cl | $CH_3$ | H | Cl |
| 63 | Q-3 | Cl | $CH_2C\equiv CH$ | H | Cl |
| 64 | Q-3 | Cl | $CH_2C\equiv CH$ | $CH_3$ | Cl |
| 65 | Q-4 | Cl | $CH_3$ | H | H |
| 66 | Q-4 | Cl | $C_2H_5$ | H | H |
| 67 | Q-4 | Cl | $n\text{-}C_3H_7$ | H | H |
| 68 | Q-4 | Cl | $i\text{-}C_3H_7$ | H | H |
| 69 | Q-4 | Br | $n\text{-}C_4H_9$ | H | H |
| 70 | Q-4 | Cl | $CH_2CH=CH_2$ | H | H |
| 71 | Q-4 | Cl | $CH_2C\equiv CH$ | H | H |
| 72 | Q-4 | Cl | $CH(CH_3)C\equiv CH$ | H | H |

TABLE 1-continued

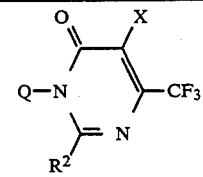

| Compound No. | Q | A | R¹ | R² | X |
|---|---|---|---|---|---|
| 73 | Q-4 | Cl | $CH_2CH_2F$ | H | H |
| 74 | Q-4 | Cl | $CH_2CH_2CH_2F$ | H | H |
| 75 | Q-4 | Cl | $CH_2OCH_3$ | H | H |
| 76 | Q-4 | Cl | $CH_3$ | $CH_3$ | H |
| 77 | Q-4 | Cl | $C_2H_5$ | $CH_3$ | H |
| 78 | Q-4 | Cl | $i\text{-}C_3H_7$ | $CH_3$ | H |
| 79 | Q-4 | Cl | $CH_2CH=CH_2$ | $CH_3$ | H |
| 80 | Q-4 | Cl | $CH_2C\equiv CH$ | $CH_3$ | H |
| 81 | Q-4 | Cl | $CH_2CH_2F$ | $CH_3$ | H |
| 82 | Q-4 | Cl | $CH_3$ | H | $CH_3$ |
| 83 | Q-4 | Cl | $C_2H_5$ | H | $CH_3$ |
| 84 | Q-4 | Cl | $i\text{-}C_3H_7$ | H | $CH_3$ |
| 85 | Q-4 | Cl | $CH_2C\equiv CH$ | H | $CH_3$ |
| 86 | Q-4 | Cl | $CH_3$ | $CH_3$ | $CH_3$ |
| 87 | Q-4 | Cl | $i\text{-}C_2H_7$ | $CH_3$ | $CH_3$ |
| 88 | Q-4 | Cl | $CH_2C\equiv CH$ | $CH_3$ | $CH_3$ |
| 89 | Q-4 | Cl | $CH_3$ | H | Cl |
| 90 | Q-4 | Cl | $i\text{-}C_3H_7$ | H | Cl |
| 91 | Q-4 | Cl | $CH_2C\equiv CH$ | H | Cl |
| 92 | Q-4 | Cl | $CH_3$ | $CH_3$ | Cl |
| 93 | Q-4 | Cl | $i\text{-}C_3H_7$ | $CH_3$ | Cl |
| 94 | Q-4 | Cl | $CH_2C\equiv CH$ | $CH_3$ | Cl |
| 95 | Q-5 | | $CH_3$ | H | H |
| 96 | Q-5 | | $C_2H_5$ | H | H |
| 97 | Q-5 | | $i\text{-}C_3H_7$ | H | H |
| 98 | Q-5 | | $sec\text{-}C_4H_9$ | H | H |
| 99 | Q-5 | | $CH_2CH=CH_2$ | H | H |
| 100 | Q-5 | | $CH_2C\equiv CH$ | H | H |
| 101 | Q-5 | | $CH(CH_3)C\equiv CH$ | H | H |
| 102 | Q-5 | | $CH_2CH_2F$ | H | H |
| 103 | Q-5 | | $CH_2CH_2Cl$ | H | H |
| 104 | Q-5 | | $CH_2CH_2CH_2F$ | H | H |
| 105 | Q-5 | | $CH_2CH_2CH_2Cl$ | H | H |
| 106 | Q-5 | | $CH_2OCH_3$ | H | H |
| 107 | Q-5 | | $CH_3$ | $CH_3$ | H |
| 108 | Q-5 | | $C_2H_5$ | $CH_3$ | H |
| 109 | Q-5 | | $i\text{-}C_3H_7$ | $CH_3$ | H |
| 110 | Q-5 | | $sec\text{-}C_4H_9$ | $CH_3$ | H |
| 111 | Q-5 | | $CH_2CH=CH_2$ | $CH_3$ | H |
| 112 | Q-5 | | $CH_2C\equiv CH$ | $CH_3$ | H |
| 113 | Q-5 | | $CH_2CH_2CH_2F$ | $CH_3$ | H |
| 114 | Q-5 | | $CH_3$ | H | $CH_3$ |
| 115 | Q-5 | | $C_2H_5$ | H | $CH_3$ |
| 116 | Q-5 | | $i\text{-}C_3H_7$ | H | $CH_3$ |
| 117 | Q-5 | | $sec\text{-}C_4H_9$ | H | $CH_3$ |
| 118 | Q-5 | | $CH_2CH=CH_2$ | H | $CH_3$ |
| 119 | Q-5 | | $CH_2C\equiv CH$ | H | $CH_3$ |
| 120 | Q-5 | | $CH_2CH_2CH_2F$ | H | $CH_3$ |
| 121 | Q-5 | | $CH_3$ | $CH_3$ | $CH_3$ |
| 122 | Q-5 | | $C_2H_5$ | $CH_3$ | $CH_3$ |
| 123 | Q-5 | | $i\text{-}C_3H_7$ | $CH_3$ | $CH_3$ |
| 124 | Q-5 | | $sec\text{-}C_4H_9$ | $CH_3$ | $CH_3$ |
| 125 | Q-5 | | $CH_2C\equiv CH$ | $CH_3$ | $CH_3$ |
| 126 | Q-5 | | $CH_2CH_2CH_2F$ | $CH_3$ | $CH_3$ |
| 127 | Q-5 | | $CH_3$ | H | Cl |
| 128 | Q-5 | | $C_2H_5$ | H | Cl |
| 129 | Q-5 | | $i\text{-}C_3H_7$ | H | Cl |
| 130 | Q-5 | | $sec\text{-}C_4H_9$ | H | Cl |
| 131 | Q-5 | | $CH_2C\equiv CH$ | H | Cl |
| 132 | Q-5 | | $CH_2CH_2CH_2F$ | H | Cl |
| 133 | Q-5 | | $CH_3$ | $CH_3$ | Cl |
| 134 | Q-5 | | $C_2H_5$ | $CH_3$ | Cl |
| 135 | Q-5 | | $i\text{-}C_3H_7$ | $CH_3$ | Cl |
| 136 | Q-5 | | $sec\text{-}C_4H_9$ | $CH_3$ | Cl |
| 137 | Q-5 | | $CH_2C\equiv CH$ | $CH_3$ | Cl |
| 138 | Q-5 | | $CH_2CH_2CH_2F$ | $CH_3$ | Cl |
| 139 | Q-5 | | $CH_3$ | H | $C_2H_5$ |
| 140 | Q-5 | | $i\text{-}C_3H_7$ | H | $C_2H_5$ |
| 141 | Q-5 | | $CH_2C\equiv CH$ | H | $C_2H_5$ |
| 142 | Q-6 | | $CH_3$ | H | H |
| 143 | Q-6 | | $C_2H_5$ | H | H |
| 144 | Q-6 | | $n\text{-}C_3H_7$ | H | H |

TABLE 1-continued

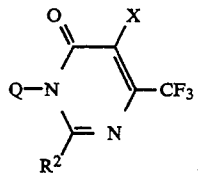

| Compound No. | Q | A | R¹ | R² | X |
|---|---|---|---|---|---|
| 145 | Q-6 | | i-C₃H₇ | H | H |
| 146 | Q-6 | | n-C₄H₉ | H | H |
| 147 | Q-6 | | sec-C₄H₉ | H | H |
| 148 | Q-6 | | CH₂CH=CH₂ | H | H |
| 149 | Q-6 | | CH₂C≡CH | H | H |
| 150 | Q-6 | | CH(CH₃)C≡CH | H | H |
| 151 | Q-6 | | CH₂CH₂F | H | H |
| 152 | Q-6 | | CH₂OCH₃ | H | H |
| 153 | Q-6 | | CH₃ | CH₃ | H |
| 154 | Q-6 | | C₂H₅ | CH₃ | H |
| 155 | Q-6 | | i-C₃H₇ | CH₃ | H |
| 156 | Q-6 | | CH₂CH=CH₂ | CH₃ | H |
| 157 | Q-6 | | CH₂C≡CH | CH₃ | H |
| 158 | Q-6 | | CH₂CH₂F | CH₃ | H |
| 159 | Q-6 | | CH₂OCH₃ | CH₃ | H |
| 160 | Q-6 | | CH₃ | H | CH₃ |
| 161 | Q-6 | | C₂H₅ | H | CH₃ |
| 162 | Q-6 | | i-C₃H₇ | H | CH₃ |
| 163 | Q-6 | | CH₂CH=CH₂ | H | CH₃ |
| 164 | Q-6 | | CH₂C≡CH | H | CH₃ |
| 165 | Q-6 | | CH₂OCH₃ | H | CH₃ |
| 166 | Q-6 | | CH₃ | CH₃ | CH₃ |
| 167 | Q-6 | | C₂H₅ | CH₃ | CH₃ |
| 168 | Q-6 | | i-C₃H₇ | CH₃ | CH₃ |
| 169 | Q-6 | | CH₂C≡CH | CH₃ | CH₃ |
| 170 | Q-6 | | CH₂OCH₃ | CH₃ | CH₃ |
| 171 | Q-6 | | CH₃ | H | Cl |
| 172 | Q-6 | | CH₂C≡CH | H | Cl |
| 173 | Q-6 | | CH₃ | CH₃ | Cl |
| 174 | Q-6 | | CH₂C≡CH | H | C₂H₅ |
| 175 | Q-7 | | CH₃ | H | H |
| 176 | Q-7 | | C₂H₅ | H | H |
| 177 | Q-7 | | n-C₃H₇ | H | H |
| 178 | Q-7 | | i-C₃H₇ | H | H |
| 179 | Q-7 | | n-C₄H₉ | H | H |
| 180 | Q-7 | | sec-C₄H₉ | H | H |
| 181 | Q-7 | | CH₂CH=CH₂ | H | H |
| 182 | Q-7 | | CH₂C≡CH | H | H |
| 183 | Q-7 | | CH(CH₃)C≡CH | H | H |
| 184 | Q-7 | | CH₂CH₂F | H | H |
| 185 | Q-7 | | CH₂CH₂Cl | H | H |
| 186 | Q-7 | | CH₂CH₂CH₂F | H | H |
| 187 | Q-7 | | CH₂CH₂CH₂Cl | H | H |
| 188 | Q-7 | | CH₂OCH₃ | H | H |
| 189 | Q-7 | | CH₃ | CH₃ | H |
| 190 | Q-7 | | C₂H₅ | CH₃ | H |
| 191 | Q-7 | | n-C₃H₇ | CH₃ | H |
| 192 | Q-7 | | i-C₃H₇ | CH₃ | H |
| 193 | Q-7 | | n-C₄H₉ | CH₃ | H |
| 194 | Q-7 | | sec-C₄H₉ | CH₃ | H |
| 195 | Q-7 | | CH₂CH=CH₂ | CH₃ | H |
| 196 | Q-7 | | CH₂C≡CH | CH₃ | H |
| 197 | Q-7 | | CH(CH₃)C≡CH | CH₃ | H |
| 198 | Q-7 | | CH₂CH₂F | CH₃ | H |
| 199 | Q-7 | | CH₂CH₂Cl | CH₃ | H |
| 200 | Q-7 | | CH₂CH₂CH₂F | CH₃ | H |
| 201 | Q-7 | | CH₂CH₂CH₂Cl | CH₃ | H |
| 202 | Q-7 | | CH₂OCH₃ | CH₃ | H |
| 203 | Q-7 | | CH₃ | H | CH₃ |
| 204 | Q-7 | | C₂H₅ | H | CH₃ |
| 205 | Q-7 | | n-C₃H₇ | H | CH₃ |
| 206 | Q-7 | | i-C₃H₇ | H | CH₃ |
| 207 | Q-7 | | n-C₄H₉ | H | CH₃ |
| 208 | Q-7 | | sec-C₄H₉ | H | CH₃ |
| 209 | Q-7 | | CH₂CH=CH₂ | H | CH₃ |
| 210 | Q-7 | | CH₂C≡CH | H | CH₃ |
| 211 | Q-7 | | CH(CH₃)C≡CH | H | CH₃ |
| 212 | Q-7 | | CH₂CH₂F | H | CH₃ |
| 213 | Q-7 | | CH₂CH₂Cl | H | CH₃ |
| 214 | Q-7 | | CH₂CH₂CH₂F | H | CH₃ |
| 215 | Q-7 | | CH₂CH₂CH₂Cl | H | CH₃ |
| 216 | Q-7 | | CH₂OCH₃ | H | CH₃ |

TABLE 1-continued

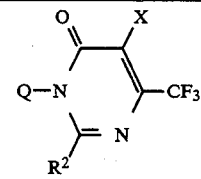

| Compound No. | Q | A | R¹ | R² | X |
|---|---|---|---|---|---|
| 217 | Q-7 | | CH₃ | CH₃ | CH₃ |
| 218 | Q-7 | | C₂H₅ | CH₃ | CH₃ |
| 219 | Q-7 | | n-C₃H₇ | CH₃ | CH₃ |
| 220 | Q-7 | | i-C₃H₇ | CH₃ | CH₃ |
| 221 | Q-7 | | n-C₄H₉ | CH₃ | CH₃ |
| 222 | Q-7 | | sec-C₄H₉ | CH₃ | CH₃ |
| 223 | Q-7 | | CH₂CH=CH₂ | CH₃ | CH₃ |
| 224 | Q-7 | | CH₂C≡CH | CH₃ | CH₃ |
| 225 | Q-7 | | CH₂CH₂F | CH₃ | CH₃ |
| 226 | Q-7 | | CH₂CH₂CH₂F | CH₃ | CH₃ |
| 227 | Q-7 | | CH₂OCH₃ | CH₃ | CH₃ |
| 228 | Q-7 | | CH₃ | H | Cl |
| 229 | Q-7 | | C₂H₅ | H | Cl |
| 230 | Q-7 | | i-C₃H₇ | H | Cl |
| 231 | Q-7 | | sec-C₄H₉ | H | Cl |
| 232 | Q-7 | | CH₂CH=CH₂ | H | Cl |
| 233 | Q-7 | | CH₂C≡CH | H | Cl |
| 234 | Q-7 | | CH₂CH₂F | H | Cl |
| 235 | Q-7 | | CH₂OCH₃ | H | Cl |
| 236 | Q-7 | | CH₃ | CH₃ | Cl |
| 237 | Q-7 | | i-C₃H₇ | CH₃ | Cl |
| 238 | Q-7 | | CH₂C≡CH | CH₃ | Cl |
| 239 | Q-7 | | CH₃ | H | C₂H₅ |
| 240 | Q-7 | | i-C₃H₇ | H | C₂H₅ |
| 241 | Q-7 | | CH₂C≡CH | H | C₂H₅ |
| 242 | Q-7 | | i-C₃H₇ | CH₃ | C₂H₅ |
| 243 | Q-7 | | CH₂C≡CH | CH₃ | C₂H₅ |
| 244 | Q-8 | | CH₃ | H | H |
| 245 | Q-8 | | C₂H₅ | H | H |
| 246 | Q-8 | | n-C₃H₇ | H | H |
| 247 | Q-8 | | i-C₃H₇ | H | H |
| 248 | Q-8 | | n-C₄H₉ | H | H |
| 249 | Q-8 | | sec-C₄H₉ | H | H |
| 250 | Q-8 | | CH₂CH=CH₂ | H | H |
| 251 | Q-8 | | CH₂C≡CH | H | H |
| 252 | Q-8 | | CH(CH₃)C≡CH | H | H |
| 253 | Q-8 | | CH₂CH₂F | H | H |
| 254 | Q-8 | | CH₂CH₂CH₂F | H | H |
| 255 | Q-8 | | CH₂OCH₃ | H | H |
| 256 | Q-8 | | CH₃ | CH₃ | H |
| 257 | Q-8 | | i-C₃H₇ | CH₃ | H |
| 258 | Q-8 | | CH₂C≡CH | CH₃ | H |
| 259 | Q-8 | | CH₂CH₂F | CH₃ | H |
| 260 | Q-8 | | CH₂OCH₃ | CH₃ | H |
| 261 | Q-8 | | CH₃ | H | CH₃ |
| 262 | Q-8 | | i-C₃H₇ | H | CH₃ |
| 263 | Q-8 | | CH₂C≡CH | H | CH₃ |
| 264 | Q-8 | | CH₂CH₂F | H | CH₃ |
| 265 | Q-8 | | CH₂OCH₃ | H | CH₃ |
| 266 | Q-8 | | CH₃ | CH₃ | CH₃ |
| 267 | Q-8 | | i-C₃H₇ | CH₃ | CH₃ |
| 268 | Q-8 | | CH₂C≡CH | CH₃ | CH₃ |
| 269 | Q-8 | | CH₂CH₂F | CH₃ | CH₃ |
| 270 | Q-8 | | CH₂OCH₃ | CH₃ | CH₃ |
| 271 | Q-8 | | CH₃ | H | Cl |
| 272 | Q-8 | | i-C₃H₇ | H | Cl |
| 273 | Q-8 | | CH₂C≡CH | H | Cl |
| 274 | Q-8 | | CH₃ | CH₃ | Cl |
| 275 | Q-8 | | i-C₃H₇ | CH₃ | Cl |
| 276 | Q-8 | | CH₂C≡CH | CH₃ | Cl |
| 277 | Q-8 | | CH₂C≡CH | H | C₂H₅ |
| 278 | Q-9 | | CH₃ | H | H |
| 279 | Q-9 | | C₂H₅ | H | H |
| 280 | Q-9 | | n-C₃H₇ | H | H |
| 281 | Q-9 | | i-C₃H₇ | H | H |
| 282 | Q-9 | | n-C₄H₉ | H | H |
| 282 | Q-9 | | sec-C₄H₉ | H | H |
| 284 | Q-9 | | CH₂CH₂F | H | H |
| 285 | Q-9 | | CH₂OCH₃ | H | H |
| 286 | Q-9 | | CH₃ | CH₃ | H |
| 287 | Q-9 | | C₂H₅ | CH₃ | H |
| 288 | Q-9 | | i-C₃H₇ | CH₃ | H |

TABLE 1-continued

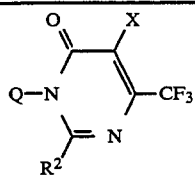

| Compound No. | Q | A | R¹ | R² | X |
|---|---|---|---|---|---|
| 289 | Q-9 | | $CH_2OCH_3$ | $CH_3$ | H |
| 290 | Q-9 | | $CH_3$ | H | $CH_3$ |
| 291 | Q-9 | | $C_2H_5$ | H | $CH_3$ |
| 292 | Q-9 | | $i\text{-}C_3H_7$ | H | $CH_3$ |
| 293 | Q-9 | | $CH_2OCH_3$ | H | $CH_3$ |
| 294 | Q-9 | | $CH_3$ | $CH_3$ | $CH_3$ |
| 295 | Q-9 | | $i\text{-}C_3H_7$ | $CH_3$ | $CH_3$ |
| 296 | Q-9 | | $CH_3$ | H | Cl |
| 297 | Q-9 | | $i\text{-}C_3H_7$ | H | Cl |
| 298 | Q-9 | | $CH_3$ | $CH_3$ | Cl |
| 299 | Q-9 | | $i\text{-}C_3H_7$ | $CH_3$ | Cl |
| 300 | Q-9 | | $CH_3$ | H | $C_2H_5$ |
| 301 | Q-9 | | $i\text{-}C_3H_7$ | H | $C_2H_5$ |

The compounds (I) of the present invention have excellent herbicidal activity and some of the compounds (I) have excellent selectivity between crop plants and weeds. In other words, the compounds (I) of the present invention can exhibit herbicidal activity against various unfavorable weeds under the foliar treatment or soil treatment on upland fields. The compounds (I) of the present invention can also exhibit herbicidal activity against various unfavorable weeds under the flooding treatment on paddy fields.

Examples of the weeds which can be controlled or exterminated by the compounds (I) of the present invention are broad-leaved weeds such as wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), wild radish (*Raphanus raphanistrum*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), purple deadnettle (*Lamium pupureum*), henbit (*Lamium amplexicaure*), Jimsonweed (*Datura stramonium*), black nightshade (*Solanum nigrum*), Persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), sun spurge (*Euphorbia helioscopia*) and spotted spurge (*Euphorbia maculata*); gramineous weeds such as Japanese millett (*Echinochloa frumentacea*), barnyardgrass (*Echinochloa crus-galli*), green foxtail (*Setaria viridis*), southern crabgrass (*Digitaria ciliaris*), annual bluegrass (*Poa annua*), blackgrass (*Alopecurus myosuroides*), wild oats (*Avena fatua*), Johnsongrass (*Sorghum halepense*), quackgrass (*Agropron repens*), downy brome (*Bromus tectorum*) and giant foxtail (*Setaria faberi*); commelinaceous weeds such as Asiatic dayflower (*Commelina communis*); and cyperaceous weeds such as rice flatsedge (*Cyperus iria*). Some of the compounds (I) of the present invention exhibit no material phytotoxicity on main crops such as corn, wheat, rice plant, soybean and cotton under the soil treatment.

The compounds (i) of the present invention have herbicidal activity against various unfavorable weeds under the flooding treatment on paddy fields, examples of which are gramineous weeds such as barnyard grass (*Echinochloa oryzoides*); broad-leaved weeds such as common falsepimpernel (*Lindernia procumbens*), Indian toothcup (*Rotala indica*) and waterwort (*Elatine triandra*); cyperaceous weeds such as hardstem bulrush (*Scirpus juncoides*), needle spikerush (*Eleocharis acicularis*), and water nutgrass (*Cyperus serotinus*); and others such as arrowhead (*Sagittaria pygmaea*), while they exhibit no material phytotoxicity on rice plant.

When the compound (I) of the present invention is used as an active ingredient of herbicides, it is usually formulated with solid or liquid carries or diluents as well as surfactants and other auxiliary agents into conventional formulations such as emulsifiable concentrates, wettable powders, flowables, granules and water-dispersible granules.

These formulations contain the compound (I) as an active ingredient at a content within the range of 0.005% to 80% by weight, preferably from 0.01% to 70% by weight, based on the total weight of each of the formulations.

Examples of the solid carrier or diluent are fine powders or granules of kaolin clay, attapulgite clay, bentonite, terra alba, pyrophyllite, talc, diatomaceous earth, calcite, walnut shell powder, urea, ammonium sulfate and synthetic hydrous silicate. As the liquid carrier or diluent, there can be exemplified aromatic hydrocarbons such as xylene and methylnaphthalene; alcohols such as isopropanol, ethylene glycol and 2-ethoxyethanol; ketones such as acetone, cyclohexanone and isophorone; vegetable oils such as soybean oil and cotton seed oil; dimethylsulfoxide, N,N-dimethylormamide, acetonitrile, water and the like.

Examples of the surfactant used for emulsification, dispersing or spreading are those of anionic type, such as alkylsulfates, alkylsulfonates, alkylarylsulfonates, dialkylsulfosuccinates and phosphates of polyoxyethylene alkylaryl ether; and those of nonionic type, such as polyoxyethylene alkyl ethers, polyoxyethylene alkylaryl ethers, polyoxyethylene polyoxypropylene block copolymers, sorbitan fatty acid esters and polyoxyethylene sorbitan fatty acid esters.

Examples of the auxiliary agent are ligninsufonates, alginates, polyvinyl alcohol, gum arabic, carboxymethyl cellulose (CMC) and isopropyl acid phosphate (PAP).

The compound (I) of the present invention is usually formulated in any suitable formulation and used for pre-emergence or post-emergence control of undesired weeds by the soil or foliar treatment for upland fields and by the flooding treatment for paddy fields. The soil treatment includes soil surface treatment and soil incorporation. The foliar treatment is effected by application over the plants or by directed application to the weeds to keep any chemical off the crop foliage.

Further, the compound (I) of the present invention may be used together with any other herbicide to enhance its herbicidal activity. Moreover, it may also be used in admixture with insecticides, acaricides, nematocides, fungicides, plant growth regulators, fertilizers, soil improver and the like.

The compound (I) of the present invention can be used as an active ingredient of herbicides to be employed for paddy fields, upland fields, orchards, pasturelands, lawns, forests or non-agricultural fields.

The compound (I) of the present invention can also be used as an active ingredient of harvestaid agents such as defoliants and desiccating agents for crop plants such as cotton (*Gossypium hirsutum*) and potato (*Solanum tuberosum*).

When the compound (I) of the present invention is used as an active ingredient of herbicides, the dosage thereof is usually in the range of from 0.01 to 100 grams, preferably from 0.02 to 20 grams, per are, although it may vary depending on the prevailing weather conditions, formulation type employed, application timing, type of application, soil involved, crop and weed species, and the like. A designated amount of the compound (I) formulated in the form of an emulsifiable concentrate, wettable powder, flowable, water-dispersible granule or the like, may usually be employed by diluting it with water at a volume of about 1 to 10 liters per are, if necessary, with addition of an adjuvant such as a spreading agent. The compound (I) formulated in the form of a kind of flowable or granules may usually be applied without dilution.

Examples of the adjuvant include, in addition to the surfactants as described above, polyoxyethylene resin acids (esters), ligninsulfonates, abietates, dinaphthylmethanedisulfonates, crop oil concentrates and crop oils such as soybean oil, corn oil, cotton seed oil and sunflower oil.

The present invention will be further illustrated by the following production examples, formulation examples and test examples, which are not to be construed to limit the scope thereof.

The following will describe production examples wherein the compounds of the present invention are designated by the corresponding numbers as shown in Table 1.

PRODUCTION EXAMPLE 1

Preparation of Compound No. 117

3-(3-Sec-butyl-6-fluoro-2-oxo-benzothiazolin-5-yl)-5-methyl-2-mercapto-6-trifluoromethylpyrimidin-4-one (0.4 g), Raney nickel (2.0 g), tetrahydrofuran (20 ml) and ammonia water (10 ml) are mixed and the mixture was heated under reflux for 4 hours.

After completion of the reaction, the reaction mixture was cooled to room temperature and extracted with ethyl acetate. The extract was washed with water, dried over anhydrous magnesium sulfate, and concentrated under reduced pressure. The residue was purified by column chromatography on silica gel to give Compound No. 117 (0.3 g), m.p., 149.1° C.

$^1$H-NMR [60 MHz, CDCl$_3$]: 0.9 ppm (t, 3H, J=7 Hz), 1.5 (d, 3H, J=7 Hz), 1.7–2.2 (m, 2H), 2.2 (bs, 3H), 4.2–4.8 (m, 1H), 7.2 (d, 1H, J=6 Hz), 7.4 (d, 1H, J=10 Hz), 8.1 (bs, 1H).

According to Production Example 1, Compound No. 39 (0.1 g) was obtained by using 3-(4-chloro-5-ethoxycarbonyl-2-fluorophenyl)-5-methyl-2-mercapto-6-trifluoromethylpyrimidin-4-one (0.4 g).

$^1$H-NMR [60 MHz, CDCl$_3$]: 1.4 ppm (t, 3H, J=7 Hz), 2.3 (bs, 3H), 4.3 (q, 2H, J=7 Hz), 7.4 (d, 1H, J=10 Hz), 7.9 (d, 1H, J=6 Hz), 8.0 (bs, 1H).

PRODUCTION EXAMPLE 2

Preparation of Compound No. 233

A solution of 5-chloro-3-(7-fluoro-2,3-dihydro-3-oxo-2H-1,4-benzoxazin-6-yl)-6-trifluoromethylpyrimidin-4-one (0.36 g) in dimethylformamide (10 ml) was added dropwise to a suspension of 50% sodium hydride (0.05 g) in dimethylformamide (10 ml) at a temperature of 5° to 10° C., and the mixture was stirred at room temperature for 30 minutes. Propargylbromide (0.2 g) was added thereto, and the resultant mixture was stirred for 3 hours.

After completion of the reaction, the reaction mixture was poured into water, and the resultant mixture was extracted with ethyl acetate. The extract was dried over anhydrous magnesium sulfate, and concentrated under reduced pressure. The residue was purified by column chromatography on silica gel to give Compound No. 233 (0.3 g).

$^1$H-NMR [60 MHz, CDCl$_3$]: 2.30 ppm (t, 1H, J=2 Hz), 4.55 (d, 2H, J=2 Hz), 4.60 (s, 2H), 6,85 (d, 1H, J=10 Hz), 7.10 (d, 1H, J=6 Hz), 8,00 (bs, 1H)

PRODUCTION EXAMPLE 3

Preparation of Compound No. 3

3-(4-Amino-2-fluoro-5-isopropoxyphenyl)-6-trifluoromethylpyrimidine-4-one (1.1 g) was added to 10% hydrochloric acid (30 ml) at the room temperature, and the resultant mixture was stirred for 1 hour. The mixture was cooled to 0° C., a solution of sodium nitrite (0.247 g) in water (5 ml) was added dropwise thereto, and the resultant mixture was stirred at 0° C. for 1 hour. The mixture was added dropwise to a solution of cuprous chloride (0.355 g) in conc. hydrochloric acid (50 ml) at room temperature, and the resultant mixture was stirred at room temperature for 30 minutes.

After completion of the reaction, the reaction mixture was extracted with diethyl ether, and the extract was dried over anhydrous magnesium sulfate, and concentrated under reduced pressure. The residue was purified by column chromatography on silica gel to give Compound No. 3 (0.8 g), m.p., 142.3° C.

$^1$H-NMR [60 MHz,CDCl$_3$]: 1.35 ppm (d, 6H, J=7 Hz), 4.2–4.8 (m, 1H), 6.90 (d, 1H, J=6 Hz), 7.37 (d, 1H, J=10 Hz), 8.15 (bs, 1H)

PRODUCTION EXAMPLE 4

Preparation of Compound No. 109

To a solution of 3-(3-isopropyl-6-fluoro-2-oxobenzothiazolin-5-yl)-6-trifluoromethylpyrimidin-4-one (4.2 g) dissolved in methanol (120 ml), dimethylamine (50 ml) was added, and the resultant mixture was heated under reflux for 10 hours.

After completion of the reaction, the reaction mixture was cooled to room temperature, and concentrated under reduced pressure. The residue was purified by column chromatography on silica gel to give N-(3-isopropyl-6-fluoro-2-oxobenzothiazolin-5-yl)-3-amino-4,4,4-trifluorocrotonamide (0.8 g), m.p., 243.2 ° C.

$^1$H-NMR [60 MHz, CDCl$_3$]: 1.60 ppm (d, 6H, J=7 Hz), 4.7–5.2 (m, 1H), 5.3 (bs, 1H), 6.4–6.9 (m, 1H), 7.22 (d, 1H, J=10 Hz), 7.4–7.6 (m, 1H), 848 (d, 1H, J=6 Hz).

N-(3-isopropyl-6-fluoro-2-oxobenzothiazolin-5-yl)-3-amino-4,4,4-trifluorocrotonamide (0.8 g) was dissolved in toluene (20 ml), to which acetylchloride (0.87 g) and diisopropylethylamine (0.3 g) were added, and the resultant mixture was stirred at 90° C. for 8 hours.

After completion of the reaction, the reaction mixture was cooled to room temperature, to which water was added, and the resultant mixture was extracted with ethyl acetate. The extract was dried over anhydrous magnesium sulfate, and concentrated under reduced pressure. The residue was purified by column chromatography on silica gel to give Compound No. 109 (0.02 g).

$^1$H-NMR [60 Mz, CDCl$_3$]: 1.60 ppm (d, 6H, J=7 Hz), 2.40 (bs, 3H), 4.5–5.1 (m, 1H), 6.85 (s, 1H), 7.17 (d, 1 H, J=6 Hz), 7.5 (d, 1H, J=10 Hz).

According to Production Examples 1 to 4, some other compounds of the formula (I) were obtained, which have physical properties as shown in Table 2.

TABLE 2

| Compound No. | Physical properties |
|---|---|
| 1 | m.p., 208.5° C. |
| 5 | viscous oil |
| 12 | m.p., 110.1° C. |
| 18 | m.p., 156.8° C. |
| 38 | $^1$H-NMR [60MHz, CDCl$_3$]: 2.2(bs, 3H), 3.9(s, 3H), 7.4(d, J=10Hz, 1H), 7.9 (d, J=6Hz, 1H), 8.0(s, 1H) |
| 40 | $^1$H-NMR [60MHz, CDCl$_3$]: 1.2(d, J=6Hz, 6H), 2.2(bs, 3H), 5.1(m, 1H), 7.2(d, J=10Hz, 1H) 7.7(d, J=7Hz, 1H), 7.8(s, 1H) |
| 97 | m.p., 193.3° C. |
| 116 | m.p., 167.0° C. |
| 181 | viscous oil |
| 191 | m.p., 139.5° C. |
| 195 | m.p., 146.9° C. |
| 196 | m.p., 170.9° C. |
| 198 | m.p., 178.0° C. |
| 205 | m.p., 153.1° C. |
| 209 | m.p., 157.3° C. |
| 210 | m.p., 194.5° C. |
| 214 | m.p., 129.0° C. |
| 216 | m.p., 168.6° C. |
| 241 | m.p., 187.3° C. |

PRODUCTION EXAMPLE 5

Preparation of Compound (II)

A solution of ethyl 3-amino-4,4,4-trifluorocrotonate (7.9 g) dissolved in dimethylformamide (30 ml) was added dropwise to a suspension of 60% sodium hydride (1.6 g) in dimethylformamide (40 ml) at 10° C., and the resultant mixture was stirred at a temperature of 10° to 20° C. for 30 minutes, To the mixture, a solution of 6-fluoro-3-isopropyl-2-benzothiazolin-5-yl-isothiocyanate (10.5 g) in toluene (100 ml) was added dropwise, and the resultant mixture was stirred at room temperature for 2 hours.

After completion of the reaction, the reaction mixture was poured into dilute hydrochloric acid, and the resultant mixture was extracted with ethyl acetate. The extract was washed with water, dried over anhydrous magnesium sulfate and concentrated under reduced pressure. The residue was crystallized with diethyl ether to give 3-(6-fluoro-3-isopropyl-2-oxobenzothiazolin-5-yl)-2-mercapto-6-trifluoromethylpyrimidin-4-one (4.5 g).

$^1$H-NMR [60 MHz, CDCl$_3$]: 1.55 ppm (d, 6H, J=7 Hz), 3.7–5.0 (m, 2H), 6.27 (s, 1H), 7.0 (d, 1H, J=6 Hz), 7.25 (d, 1H, J=10 Hz).

According to Production Example 5, 3-(6-fluoro-3-sec-butyl-2-oxobenzothiazolin- 5-yl)-2-mercapto-6-trifluoromethylpyrimidin-4-one [m.p., 219° C.], 3-(6-fluoro-3-isopropyl-2-oxobenzothiazolin-5-yl)-5-methyl-2-mercapto-6-trifluoromethylpyrimidin-4-one [m.p., 100.4° C.], 3-(7-fluoro-3-oxo-4-propargyl-1,4-benzoxazin-6-yl)-2-mercapto-6-trifluoromethylpyrimidin-4-one [m.p., 177.1° C.] and 3-(4-chloro-5-ethoxycarbonyl-2-fluorophenyl)-5-methyl-2-metcapto-6-trifluoromethylpyrimidin-4-one were obtained.

PRODUCTION EXAMPLE 6

Preparation of Compound (X)

A solution of 5-chloro-6-trifluoromethylpyrimidin-4-one (8.9 g) in dimethylformamide (100 ml) was added dropwise to a suspension of sodium hydride (2 g) in dimethylformamide (50 ml) at room temperature, and the resultant mixture was stirred at room temperature for 1 hour. 3,4-Difluoronitrobenzene (10.7 g) was added thereto, and the resultant mixture was stirred at 100° C. for 3 hours.

After completion of the reaction, the reaction mixture was cooled to room temperature and added into dilute hydrochloric acid. The resultant mixture was extracted with ethyl acetate. The extract was washed with water, dried over anhydrous magnesium sulfate, and concentrated under reduced pressure. The residue was purified by column chromatography on silica gel to give 5-chloro-3-(2-fluoro-4-nitrophenyl)-6-trifluoromethylpyrimidin-4-one (4.7 g), m.p., 162.2° C.

PRODUCTION EXAMPLE 7

Preparation of Compound (XI)

Electrolytic iron powder (4.87 g) was suspended in a mixture of acetic acid (34 ml) and water (34 ml). 5-Chloro-3-(2-fluoro-4-nitrophenyl)-6-trifluoromethylpyrimidin-4-one (4.7 g) was added slowly to this suspension at 80° C., and the resultant mixture was stirred for 30 minutes.

After completion of the reaction, the reaction mixture was cooled to room temperature and filtered to remove the excess iron. The filtrate was extracted with ethyl acetate, and the extract was washed with water and saturated aqueous sodium hydrogencarbonate, dried over anhydrous magnesium sulfate, and concentrated under reduced pressure. The residue was purified by column chromatography on silica gel to give 3-(4-amino-2-fluorophenyl)-5-chloro-6-trifluoromethylpyrimidin-4-one (4.0 g), m.p., 114.5° C.

PRODUCTION EXAMPLE 8

Preparation of Compound (XII)

3-(4-Amino-2-fluorophenyl)-5-chloro-6-trifluoromethylpyrimidin-4-one (3.0 g) was suspended in a mixture of sulfuric acid (14.7 g) and water (160 ml), and the resultant mixture was stirred at 80° C. for 1 hour, followed by cooling to 0° C. A solution of sodium nitrite (0.71 g) in water (10 ml) was added dropwise to this mixture below 10° C., and the resultant mixture was stirred at a temperature of 0° to 10° C. for 30 minutes. The above mixture was added dropwise to a solution of sodium sulfate (15 g) in water (150 ml) at a temperature of 95° to 105° C., and the resultant mixture was stirred at 100° C. for 15 minutes.

After completion of the reaction, the reaction mixture was cooled to room temperature and extracted with ethyl acetate. The extract was washed with water, dried over anhydrous magnesium sulfate, and concentrated under reduced pressure. The residue was purified by column chromatography on silica gel to give 5-chloro-3-(2-fluoro-4-hydroxyphenyl)-6-trifluoromethylpyrimidin-4-one (0.8 g), m.p., 192.5° C.

PRODUCTION EXAMPLE 9

Preparation of Compound (XIII)

Fuming nitric acid (0.36 g) was added to a solution of 5-chloro-3-(2-fluoro-4-hydroxyphenyl)-6-trifluoromethylpyrimidin-4-one (0.8 g) in chloroform (5 ml) at 10° C., to which methylene chloride (200 ml) was added, and the resultant mixture was stirred overnight at room temperature.

After completion of the reaction, the reaction mixture was washed with water, dried over anhydrous magnesium sulfate, and concentrated under reduced pressure. The residue was purified by column chromatography on silica gel to give 5-chloro-3-(2-fluoro-4-hydroxy-5-nitrophenyl)-6-trifluoromethylpyrimidin-4-one (0.8 g).

$^1$H-NMR [60 MHz, CDCl$_3$]: 7.10 ppm (d, 1H, J=10 Hz), 8.05 (bs, 1H), 8.25 (d, 1H, J=6 Hz).

PRODUCTION EXAMPLE 10

Preparation of Compound (XIV)

Ethyl bromoacetate (0.46 g) was added to a suspension of 5-chloro-3-(2-fluoro-4-hydroxy-5-nitrophenyl)-6-trifluoromethylpyrimidin-4one-(0.8 g) and anhydrous potassium carbonate powder (0.47 g) in dimethylformamide (15 ml) at room temperature, and the resultant mixture was stirred at a temperature of 40° to 50° C. for 2 hours.

After completion of the reaction, the reaction mixture was poured into water and extracted with ethyl acetate. The extract was washed with water, dried over anhydrous magnesium sulfate, and concentrated under reduced pressure. The residue was purified by column chromatography on silica gel to give 5-chloro-3-(2-fluoro-4-ethoxycarbonylmethoxy-5-nitrophenyl)-6-trifluoromethylpyrimidin-4-one (0.8 g).

$^1$H-NMR [60 MHz, CDCl$_3$]: 1.25 ppm (t, 3H, J=6 Hz), 4.20 (q, 2H, J=6 Hz), 4.75 (s, 2H), 6.88 (d, 1H, J=10 Hz), 8.0 (d, 1H, J=6 Hz), 8.1 (bs, 1H).

PRODUCTION EXAMPLE 11

Preparation of Compound (XVI)

A solution of ethyl 3-amino-4,4,4-trifluoro-2-methylcrotonate (19 g) in dimethylformamide (100 ml) was added dropwise to a suspension of 60% sodium hydride (4.0 g) in dimethylformamide (40 ml) at 10° C., and the resultant mixture was stirred at a temperature of 10° to 20° C. for 30 minutes. A solution of 2,4-difluorophenylisothiocyanate (17 g) in toluene (100 ml) was added dropwise thereto, and the resultant mixture was stirred at room temperature for 2 hours.

After completion of the reaction, the reaction mixture was poured into dilute hydrochloric acid, and the resultant mixture was extracted with ethyl acetate. The extract was washed with water, dried over anhydrous magnesium sulfate, and concentrated under reduced pressure. The residue was crystallized from diethyl ether to give 3-(2,4-difluorophenyl)-5-methyl-2-mercapto-6-trifluoromethylpyrimidin-4-one (22.5 g).

PRODUCTION EXAMPLE 12

Preparation of Compound (XVII)

3-(2,4-Difluorophenyl)-5-methyl-2-mercapto-6-trifluoromethylpyrimidin-4-one (35.7 g), Raney nickel (45 g), methanol (50 ml) and ammonia water (13 ml) was mixed together, and the mixture was heated under reflux for 5 hours.

After completion of the reaction, the reaction mixture was cooled to room temperature and extracted with ethyl acetate. The extract was washed with water, dried over anhydrous magnesium sulfate, and concentrated under reduced pressure. The residue was purified by column chromatography on silica gel to give 3-(2,4-difluorophenyl)-5-methyl-6-trifluoromethylpyrimidin-4-one (17.2 g), m.p., 137.3° C.

$^1$H-NMR [60 MHz, CDCl$_3$]: 2.30 (bs, 3H), 6.7-7.6 (m, 3H), 8.0 (bs, 1H).

According to Production Example 12, 3-(2,4-difluorophenyl)-5-ethyl-6-trifluoromethylpyrimidin-4-one [m.p., 144-145.5° C.] was obtained by using 3-(2,4-difluorophenyl)-5-ethyl-2-mercapto-6-trifluoromethylpyrimidin-4-one.

PRODUCTION EXAMPLE 13

Preparation of Compound (XVII)

Fuming nitric acid (1.63 g) was added to a solution of 3-(2,4-difluorophenyl)-5-methyl-6-trifluoromethylpyrimidin-4-one (7.5 g) in conc. sulfuric acid (50 g) at 10° C. The reaction mixture was poured into water, and the resultant mixture was extracted with ethyl acetate. The extract was washed with water, dried over anhydrous magnesium sulfate, and concentrated under reduced pressure. The residue was crystallized from diethyl ether to give 3-(2,4-difluoro-5-nitrophenyl)-5-methyl-6-trifluoromethylpyrimidine-4-one (6.4 g), m.p. 156.7° C.

$^1$H-NMR [60 MHz, CDCl$_3$/d$_6$DMSO]: 2.30 (bs, 3H), 7.40 (t, 1H, J=10 Hz), 8.20 (bs, 1H), 8.4 (t, 1H, J=6 Hz).

According to Production Example 13, 3-(2,4-difluoro-5-nitrophenyl)-5-ethyl-6-trifluoromethylpyrimidin-4-one [m.p., 145.3° C.] was obtained by using 3-(2,4-difluorophenyl)-5-ethyl-6-trifluoromethylpyrimidin-4-one.

PRODUCTION EXAMPLE 14

Preparation of Compound (XIV)

3-(2,4-Difluoro-5-nitrophenyl)-5-methyl-6-trifluoromethylpyrimidin-4-one (6.4 g), butyl glycolate (4.2 g) and potassium fluoride (3.3 g) were suspended in 1,4-dioxane (10 ml), and the suspension was refluxed with stirring for 2 days.

After completion of the reaction, the reaction mixture was cooled to room temperature and filtered to remove undissolved materials. Ethyl acetate was added to the filtrate, and the resultant mixture was washed with water, dried over anhydrous magnesium sulfate, and concentrated under reduced pressure. The residue was purified by column chromatography on silica gel to give 3-(4-butoxycarbonylmethoxy-2-fluoro-5-nitrophenyl)-5-methyl-6-trifluoromethylpyrimidin-4one (6.2 g).

PRODUCTION EXAMPLE 15

Preparation of Compound (VI)

A solution of 5-chloro-3-(2-fluoro-4-ethoxycarbonylmethoxy-5-nitrophenyl)-6-trifluoromethylpyrimidin-4-one (0.8 g) in ethyl acetate (20 ml) was added dropwise to a suspension of electrolytic iron powder (2.0 g) in 50% aqueous acetic acid (50 ml) at a temperature of 70° to 90° C., and the resultant mixture was stirred at the same temperature for 1 hour.

After completion of the reaction, the reaction mixture was cooled to room temperature, to which ethyl acetate was added, and filtered to remove the excess iron. The filtrate was separated, and the organic layer was washed with water, dried over anhydrous magnesium sulfate, and concentrated under reduced pressure. The residue was purified by column chromatography on silica gel to give 5-chloro-3-(7-fluoro-3-oxo-1,4-benzoxazin-6-yl)-6-trifluoromethylpyrimidin-4-one (0.5 g).

$^1$H-NMR [60 MHz, CDCl$_3$/d$_6$DMSO]: 4.60 ppm (s, 2H), 6.86 (d, 1H, J=10 Hz), 7.05 (d, 1H, J=6 Hz), 7.3–7.5 (m, 1H), 8.20 (bs, 1H).

According to Production Example 15, 3-(7-fluoro-3-oxo-1,4-benzoxazin-6-yl)-5-methyl-6-trifluoromethylpyrimidin-4-one [m.p., 236.8° C.] and 3-(7-fluoro-3-oxo-1,4-benzoxazin-6-yl)-5-ethyl-6-trifluoromethylpyrimidin-4-one [m.p., 172.1 ° C.] were obtained by using 3-(4-butoxycarbonylmethoxy-2-fluoro-5-nitrophenyl)-5-methyl-6-trifluoromethylpyrimidin-4-one and 3-(4-butoxycarbonylmethoxy-2-fluoro-5-nitrophenyl)-5-ethyl-6-trifluoromethylpyrimidin-4-one, respectively.

PRODUCTION EXAMPLE 16

Preparation of Compound (XXVI)

A solution of 6-trifluoromethylpyrimidin-4-one (8.2 g) in dimethylformamide (160 ml) was added dropwise to a suspension of sodium hydride (2.0 g) in demethylformamide (100 ml) at room temperature, and the resultant mixture was stirred at room temperature for 1 hour. To the mixture, methyl 3,4-difluoro-6-nitrophenylcarbonate (12 g) was added, and the resultant mixture was stirred at 100° C. for 3 hours.

After completion of the reaction, the reaction mixture was cooled to room temperature and poured into water. The resultant mixture was extracted with ethyl acetate. The extract was washed with water, dried over anhydrous magnesium sulfate, and concentrated under reduced pressure. The residue was purified by column chromatography on silica gel to give 3-(2-fluoro- 5-hydroxy-4-nitrophenyl)-6 -tri-fluoromethylpyrimidin-4-one (3.0 g), m.p., 129.1 ° C.

PRODUCTION EXAMPLE 17

Preparation of Compound (XXVII)

3-(2-Fluoro-5-hydroxy-4-nitrophenyl)-6-trifluoromethylpyrimidin-4-one (3.0 g) and potassium carbonate (2.0 g) were suspended in dimethylformamide (30 ml), to which isopropyl iodide (2.04 g) was added at room temperature, and the resultant mixture was stirred at 60° C. for 4 hours.

After completion of the reaction, the reaction mixture was cooled to room temperature and extracted with ethyl acetate. The extract was washed with water, dried over anhydrous magnesium sulfate, and concentrated under reduced pressure. The residue was purified by column chromatography on silica gel to give 3-(2-fluoro-5-isopropoxy-4-nitrophenyl)-6-trifluoromethylpyrimidin-4-one (3.3 g).

$^1$H-NMR [60 MHz, CDCl$_3$]: 1.40 ppm (d, 6H, J=7 Hz), 4.4–4.8 (m, 1H), 6.9 (s, 1H), 7.1 (d, 1H, J=6 Hz), 7.7 (d, 1H, J=10 Hz), 8.15 (bs, 1H).

According to Production Example 17, 3-(2-fluoro-5-methoxy-4-nitrophenyl)-6-trifluoromethylpyrimidin-4-one [m.p., 173.2° C. (decomp.)] and 3-(2-fluoro-4-nitro-5-propargyloxyphenyl)-6-trifluoromethylpyrimidin-4-one were obtained.

PRODUCTION EXAMPLE 18

Preparation of Compound (XXI)

Electrolytic iron powder (4.87 g) was suspended in a mixture of acetic acid (34 ml) and water (34 ml), to which 3-(2-fluoro-5-isopropoxy-4-nitrophenyl)-6-trifluoromethylpyrimidin-4-one (4.7 g) was added slowly, and the resultant mixture was stirred for 30 minutes.

After completion of the reaction, the reaction mixture was cooled to room temperature and filtered to remove the excess iron. The filtrate was extracted with ethyl acetate. The extract was washed with water and saturated aqueous sodium hydrogencarbonate, dried over anhydrous magnesium sulfate and concentrated under reduced pressure. The residue was purified by column chromatography on silica gel to give 3-(4-amino-2-fluoro-5-isopropoxyphenyl)-6-trifluoromethylpyrimidin-4-one (4.0 g).

According to Production Example 18, 3-(4-amino-2-fluoro-5-methoxyphenyl)-6-trifluoromethylpyrimidin-4-one and 3-(4-amino-2-fluoro-5-propargyloxyphenyl)-6-trifluoromethylpyrimidin-4-one were obtained by using 3-(2-fluoro-5-methoxy-4-nitrophenyl)-6-trifluoromethylpyrimidin-4-one and 3-(2-fluoro-5-propargyloxy-4-nitrophenyl)-6-trifluoromethylpyrimidin-4-one, respectively.

The following will describe formulation examples wherein the compounds of the present invention are designated by the corresponding numbers as shown in Table 1 and parts are all by weight.

FORMULATION EXAMPLE 1

Fifty parts of any one of Compound Nos. 1, 3, 12, 18, 97, 116, 117, 191, 195, 196, 198, 205, 209, 210, 214, 216 and 241, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Ten parts of any one of Compound Nos. 1, 3, 5, 12, 18, 38–40, 97, 109, 116, 117, 181, 191, 195, 196, 198, 205, 209, 210, 214, 216, 233 and 241, 14 parts of polyoxyethylene styryl phenyl ether, 6 parts of calcium dodecylbenzenesulfonate, 30 parts of xylene and 40 parts of cyclohexanone are well mixed to obtain an emulsifiable concentrate.

FORMULATION EXAMPLE 3

Two parts of any one of Compound Nos. 1, 3, 5, 12, 18, 38–40, 97, 109, 116, 117, 181, 191, 195, 196, 198, 205, 209, 210, 214, 216, 233 and 241, 1 part of synthetic hydrous silicate, 2 parts of calcium ligninsulfonate, 30 parts of bentonite and 65 parts of kaoline clay are well mixed while being powdered. The mixture is then kneaded with water, granulated and dried to obtain granules.

FORMULATION EXAMPLE 4

Twenty five parts of any one of Compound Nos. 1, 3, 12, 18, 97, 116, 117, 191, 195, 196, 198, 205, 209, 210, 214, 216 and 241, 3 parts of polyoxyethylene sorbitan monooleate, 3 parts of CMC and 69 parts of water are well mixed, and mixture was then pulverized until the particle size thereof becomes not greater than 5 microns to obtain a flowable.

The following will describe test examples wherein the compounds of the present invention are designated by the corresponding numbers as shown in Table 1.

The herbicidal activity on weeds and the phytotoxicity to crop plants were determined by visual observation as to the degree of germination and growth of the test plants (i.e., weeds and crop plants), and rated with an index 0, 1, 2, 3, 4, or 5, the numeral "0" indicating little or no material difference as seen in comparison with the untreated plants and the numeral "5" indicating the complete death of the test plants or the complete inhibition of their germination or growth.

TEST EXAMPLE 1:

Cylindrical plastic pots (diameter, 10 cm; height, 10 cm) were filled with upland field soil, and the seeds of Japanese millet, tall morningglory and velvetleaf were sowed therein and covered with soil. A designated amount of the test compound formulated in an emulsifiable concentrate as described in Formulation Example 2 was diluted with water, and the dilution was sprayed onto the soil surface by means of a small sprayer at a spray volume of 10 liters per are. The test plants were grown in a greenhouse for 19 days, and the herbicidal activity was examined. The results are shown in Table 3.

TABLE 3

| Compound No. | Dosage (g/are) | Herbicidal activity | | |
|---|---|---|---|---|
| | | Japanese millet | Tall morningglory | Velvetleaf |
| 1 | 5 | 5 | 5 | 5 |
| 3 | 5 | 5 | 5 | 5 |
| 5 | 5 | 5 | 5 | 5 |
| | 1.25 | 5 | 5 | 5 |
| 12 | 5 | 4 | 5 | 5 |
| 18 | 5 | 5 | 5 | 5 |
| | 1.25 | 5 | 5 | 5 |
| 38 | 5 | 5 | 5 | 5 |
| | 1.25 | 5 | 5 | 5 |
| 39 | 5 | 5 | 4 | 5 |
| 40 | 5 | 5 | 4 | 5 |
| 97 | 5 | 5 | 5 | 5 |
| | 1.25 | 4 | 4 | 4 |
| 109 | 5 | 5 | 5 | 5 |
| | 1.25 | 5 | 5 | 5 |
| 116 | 5 | 5 | 5 | 5 |
| | 1.25 | 5 | 5 | 5 |
| 117 | 5 | 5 | 5 | 5 |
| | 1.25 | 5 | 5 | 5 |
| 181 | 5 | 5 | 5 | 5 |
| | 1.25 | 5 | 5 | 5 |
| 191 | 5 | 5 | 5 | 5 |
| | 1.25 | 5 | 5 | 5 |
| 195 | 5 | 5 | 5 | 5 |
| | 1.25 | 5 | 5 | 5 |
| 196 | 5 | 5 | 5 | 5 |
| | 1.25 | 5 | 5 | 5 |
| 198 | 5 | 5 | 5 | 5 |
| | 1.25 | 5 | 5 | 5 |
| 205 | 5 | 5 | 5 | 5 |
| | 1.25 | 5 | 5 | 5 |
| 209 | 5 | 5 | 5 | 5 |
| | 1.25 | 5 | 5 | 5 |
| 210 | 5 | 5 | 5 | 5 |
| | 1.25 | 5 | 5 | 5 |
| 214 | 5 | 5 | 5 | 5 |
| | 1.25 | 5 | 5 | 5 |
| 216 | 5 | 5 | 5 | 5 |
| | 1.25 | 5 | 5 | 5 |
| 233 | 5 | 5 | 5 | 5 |
| | 1.25 | 5 | 5 | 5 |
| 241 | 5 | 5 | 4 | 5 |

TEST EXAMPLE 2:

Cylindrical plastic pots (diameter, 10 cm; height, 10 cm) were filled with upland field soil, and the seeds of wild radish and velvetleaf were sowed therein, and cultivated in a greenhouse for 8 days. A designated amount of the test compound formulated in an emulsifiable concentrate as described in Formulation Example 2 was diluted with water containing a spreading agent, and the dilution was sprayed over the foliage of the test plants by means of a small sprayer at a spray volume of 10 liters per are. The test plants were further grown in the greenhouse for 19 days, and the herbicidal activity was examined. The results are shown in Table 4.

TABLE 4

| Compound No. | Dosage (g/are) | Herbicidal activity | |
|---|---|---|---|
| | | Wild Radish | Velvetleaf |
| 1 | 5 | 4 | 5 |
| 3 | 5 | 5 | 5 |
| 5 | 5 | 5 | 5 |
| 12 | 5 | 5 | 5 |
| 18 | 5 | 5 | 5 |
| 38 | 5 | 5 | 5 |
| 39 | 5 | 5 | 5 |
| 40 | 5 | 5 | 5 |
| 97 | 5 | 5 | 5 |
| 109 | 5 | 5 | 5 |
| 116 | 5 | 5 | 5 |
| 117 | 5 | 5 | 5 |
| 181 | 5 | 5 | 5 |
| 191 | 5 | 5 | 5 |
| 195 | 5 | 5 | 5 |
| 196 | 5 | 5 | 5 |
| 198 | 5 | 4 | 5 |
| 205 | 5 | 5 | 5 |
| 209 | 5 | 5 | 5 |
| 210 | 5 | 5 | 5 |
| 214 | 5 | 5 | 5 |
| 216 | 5 | 5 | 5 |
| 233 | 5 | 5 | 5 |
| 241 | 5 | 4 | 5 |

TEST EXAMPLE 3:

Cylindrical plastic pots (diameter, 8 cm; height, 12 cm) were filled with paddy field soil, and the seeds of barnyardgrass and broad-leaved weed (common falsepimpernel, indian toothcup and waterwort) were sowed in 1 to 2 cm depth. Water was poured therein to make a flooded condition, and rice seedlings of 2-leaf stage were transplanted, and the test plants were grown in a greenhouse. After 5 days (at that time the weeds began to germinate), a designated amount of the test compound formulated in an emulsifiable concentrate as described in Formulation Example 2 was diluted with 2.5 ml of water, and the dilution was applied to the water surface. The test plants were grown in the greenhouse for an additional 19 days, and the herbicidal activity and phytotoxicity were examined. The results are shown in Table 5.

TABLE 5

| Compound No. | Dosage (g/are) | Phytotoxicity Riceplant | Herbicidal activity | |
|---|---|---|---|---|
| | | | Barnyard-grass | Broad-leaved weed |
| 1 | 2.5 | 0 | 5 | 5 |
| 3 | 0.63 | 0 | 5 | 5 |
| 5 | 0.63 | 1 | 5 | 5 |
| 12 | 2.5 | 0 | 5 | 5 |
| 18 | 0.16 | 1 | 5 | 5 |
| 38 | 0.63 | 0 | 4 | 5 |
| 39 | 0.63 | 0 | 4 | 4 |
| 40 | 0.63 | 1 | 5 | 5 |

TABLE 5-continued

| Compound No. | Dosage (g/are) | Phytotoxicity Riceplant | Herbicidal activity | |
|---|---|---|---|---|
| | | | Barnyard-grass | Broad-leaved weed |
| 97 | 2.5 | 0 | 5 | 5 |
| 109 | 0.63 | 1 | 5 | 5 |
| 116 | 0.16 | 1 | 5 | 5 |
| 117 | 0.16 | 0 | 5 | 5 |
| 181 | 0.63 | 1 | 5 | 5 |
| 195 | 0.16 | 1 | 4 | 5 |
| 209 | 0.04 | 0 | 4 | 4 |
| 210 | 0.04 | 1 | 5 | 5 |
| 233 | 0.04 | 1 | 5 | 5 |
| 241 | 2.5 | 1 | 5 | 5 |

What is claimed is:

1. A compound of the formula:

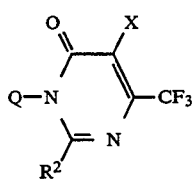

wherein $R^2$ is hydrogen or methyl; X is hydrogen, chlorine, methyl or ethyl; Q is of the formula:

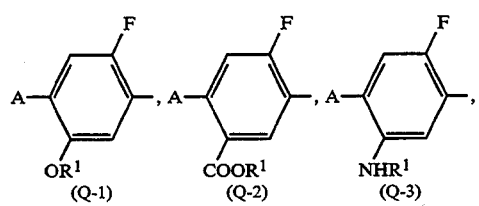

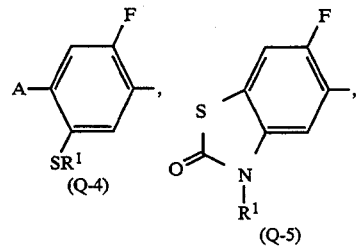

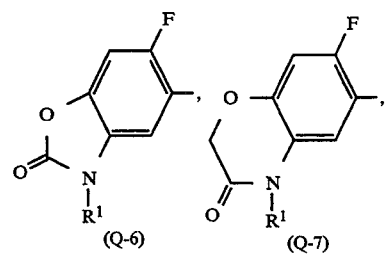

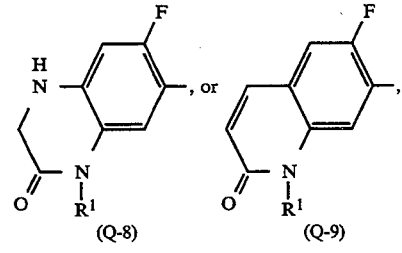

A is fluorine, chlorine or bromine; and $R^1$ is alkyl, alkenyl, alkynyl, alkoxyalkyl or haloalkyl.

2. A compound of the formula:

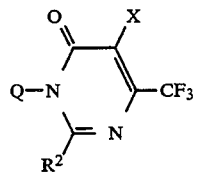

wherein $R^2$ is hydrogen or methyl; X is hydrogen, chlorine, methyl or ethyl; Q is of the formula:

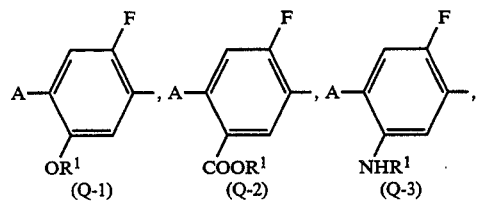

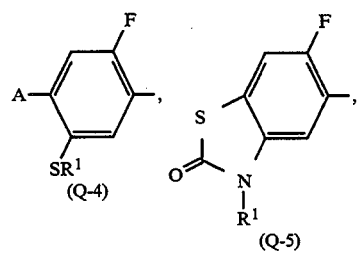

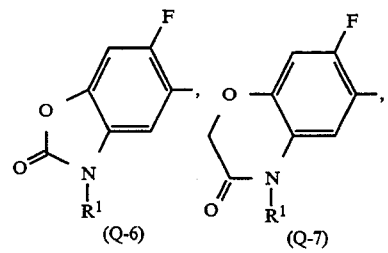

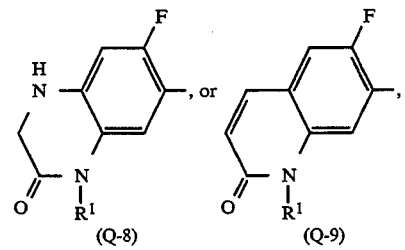

and $R^1$ is alkyl, alkenyl, alkynyl, alkoxyalkyl or haloalkyl.

3. A compound according to claim 2, wherein Q is of the formula (Q-7).

4. A herbicidal composition comprising, as an active ingredient, a herbicidally effective amount of the compound according to claim 1, and an inert carrier or diluent.

5. A compound according to claim 2, wherein Q is of the formula (Q-7) and $R^1$ is $C_1$–$C_4$ alkyl, $C_2$–$C_4$ alkenyl or $C_2$–$C_4$ alkynyl.

6. A compound according to claim 1, wherein $R^2$ is hydrogen, X is methyl, Q is of the formula Q-6 and $R^1$ is alkynyl.

7. A compound according to claim 6, wherein $R^1$ is $CH_2-C\equiv CH$.

8. A herbicidal composition comprising, as an active ingredient, a herbicidally effective amount of the compound according to claim 6, and an inert carrier or diluent.

9. A compound according to claim 2, wherein $R^2$ is methyl.

10. A compound according to claim 2, wherein X is hydrogen, chlorine or methyl.

11. A compound according to claim 2, wherein X is chlorine or methyl.

12. A compound according to claim 2, wherein X is methyl.

13. A compound which is 5-chloro-3-(7-fluoro-3,4-dihydro-3-oxo-4-propargyl-2H-1,4-benzoxazin-6-yl)-6-trifluoromethylpyrimidin-4-one.

14. A compound which is 3-(7-fluoro-3,4-dihydro-3-oxo-4-propargyl-2H-1,4-benzoxazin-6-yl)-5-methyl-6-trifluoromethyl-pyrimidin-4-one.

15. A method for exterminating undesired weeds, which comprises applying a herbicidally effective amount of the compound according to claim 1 to an area where the undesired weeds grow or would grow.

16. A herbicidal composition comprising, as an active ingredient, a herbicidally effective amount of the compound according to claim 7, and an inert carrier or diluent.

17. A method for exterminating undesired weeds, which comprises applying a herbicidally effective amount of the compound according to claim 6, to an area where the undesired weeds grow or would grow.

18. A method for exterminating undesired weeds, which comprises applying a herbicidally effective amount of the compound according to claim 7 to an area where the undesired weeds grow or would grow.

* * * * *

UNITED STATES PATENT AND TRADEMARK OFFICE
CERTIFICATE OF CORRECTION

PATENT NO. : 5,366,955
DATED : November 22, 1994
INVENTOR(S) : Eiki NAGANO, Susumu TAKEMURA, Masayuki ENOMOTO Masaharu SAKAKI and Satoru KIZAWA It is certified that error appears in the above-indentified patent and that said Letters Patent is hereby corrected as shown below:

Columns 27 and 28, lines 30-48 and 16-33, delete formulas Q-1, Q-2, Q-3, Q-4 and Q-5 from Claim 1 and from Claim 2.

Signed and Sealed this

Twenty-fifth Day of April, 1995

Attest:

BRUCE LEHMAN

*Attesting Officer*  *Commissioner of Patents and Trademarks*